(12) United States Patent
Moore et al.

(10) Patent No.: US 7,793,812 B2
(45) Date of Patent: Sep. 14, 2010

(54) DISPOSABLE MOTOR-DRIVEN LOADING UNIT FOR USE WITH A SURGICAL CUTTING AND STAPLING APPARATUS

(75) Inventors: Kyle P. Moore, Mason, OH (US); Frederick E. Shelton, IV, Hillsboro, OH (US); William B. Weisenburgh, II, Maineville, OH (US); Jerome R. Morgan, Cincinnati, OH (US); Mark H. Ransick, West Chester, OH (US); Eugene L. Timperman, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 310 days.

(21) Appl. No.: 12/031,628

(22) Filed: Feb. 14, 2008

(65) Prior Publication Data

US 2009/0206136 A1 Aug. 20, 2009

(51) Int. Cl.
*A61B 17/068* (2006.01)
(52) U.S. Cl. .................... 227/176.1; 227/19; 227/180.1
(58) Field of Classification Search .................. 227/19, 227/176.1, 175.1, 178.1, 180.1; 606/139, 606/219
See application file for complete search history.

(56) References Cited

U.S. PATENT DOCUMENTS

| | | | |
|---|---|---|---|
| 2,804,848 A | 9/1957 | O'Farrell et al. |
| 2,853,074 A | 9/1958 | Olson |
| 3,490,675 A | 1/1970 | Green et al. |
| 3,551,987 A | 1/1971 | Wilkinson |
| 3,643,851 A | 2/1972 | Green at al. |
| 3,662,939 A | 5/1972 | Bryan |
| 3,717,294 A | 2/1973 | Green |
| 3,819,100 A | 6/1974 | Noiles at al. |
| 4,331,277 A | 5/1982 | Green |
| 4,383,634 A | 5/1983 | Green |
| 4,396,139 A | 8/1983 | Hall et al. |
| 4,402,445 A | 9/1983 | Green |
| 4,415,112 A | 11/1983 | Green |
| 4,429,695 A | 2/1984 | Green |

(Continued)

FOREIGN PATENT DOCUMENTS

CA 2458946 A1 3/2003

(Continued)

OTHER PUBLICATIONS

European Search Report, Application No. 09250367.1, dated Apr. 14, 2009 (7 pages).

(Continued)

*Primary Examiner*—Scott A. Smith

(57) ABSTRACT

A self contained motor-powered disposable loading unit for use with a surgical cutting and stapling apparatus. The disposable loading unit may contain a battery that is retained in a disconnected position when the disposable loading unit is not in use and is moved to a connected position when the disposable loading unit is coupled to the surgical cutting and stapling apparatus to permit the motor to be selectively powered thereby. Indicators may be supported on the disposable loading unit to indicate when the axial drive assembly thereof is in a starting position and an ending position. Another indicator may be provided to indicate when the anvil assembly is in a closed position.

18 Claims, 7 Drawing Sheets

U.S. PATENT DOCUMENTS

| | | |
|---|---|---|
| 4,475,679 A | 10/1984 | Fleury, Jr. |
| 4,489,875 A | 12/1984 | Crawford et al. |
| 4,500,024 A | 2/1985 | DiGiovanni et al. |
| 4,505,273 A | 3/1985 | Braun et al. |
| 4,505,414 A | 3/1985 | Filipi |
| 4,506,671 A | 3/1985 | Green |
| 4,522,327 A | 6/1985 | Korthoff et al. |
| 4,530,453 A | 7/1985 | Green |
| 4,566,620 A | 1/1986 | Green et al. |
| 4,573,622 A | 3/1986 | Green et al. |
| 4,576,167 A | 3/1986 | Noiles et al. |
| 4,580,712 A | 4/1986 | Green |
| 4,610,250 A | 9/1986 | Green |
| 4,610,383 A | 9/1986 | Rothfuss et al. |
| 4,619,262 A | 10/1986 | Taylor |
| 4,629,107 A | 12/1986 | Fedotov et al. |
| 4,655,222 A | 4/1987 | Florez et al. |
| 4,664,305 A | 5/1987 | Blake, III et al. |
| 4,667,674 A | 5/1987 | Korthoff et al. |
| 4,671,445 A | 6/1987 | Barker et al. |
| 4,715,520 A | 12/1987 | Roehr, Jr. et al. |
| 4,728,020 A | 3/1988 | Green et al. |
| 4,752,024 A | 6/1988 | Green et al. |
| 4,754,909 A | 7/1988 | Barker et al. |
| 4,767,044 A | 8/1988 | Green |
| 4,805,823 A | 2/1989 | Rothfuss |
| 4,809,695 A | 3/1989 | Gwathmey et al. |
| 4,817,847 A | 4/1989 | Redtenbacher et al. |
| 4,821,939 A | 4/1989 | Green |
| 4,869,414 A | 9/1989 | Green et al. |
| 4,869,415 A | 9/1989 | Fox |
| 4,880,015 A | 11/1989 | Nierman |
| 4,941,623 A | 7/1990 | Pruitt |
| 4,944,443 A | 7/1990 | Oddsen et al. |
| 5,014,899 A | 5/1991 | Presty et al. |
| 5,042,707 A | 8/1991 | Taheri |
| 5,065,929 A | 11/1991 | Schulze et al. |
| 5,071,430 A | 12/1991 | de Salis et al. |
| 5,084,057 A | 1/1992 | Green et al. |
| 5,116,349 A | 5/1992 | Aranyi |
| 5,129,570 A | 7/1992 | Schulze et al. |
| 5,137,198 A | 8/1992 | Nobis et al. |
| 5,139,513 A | 8/1992 | Segato |
| 5,158,567 A | 10/1992 | Green |
| 5,171,247 A | 12/1992 | Hughett et al. |
| 5,171,249 A | 12/1992 | Stefanchik et al. |
| 5,209,747 A | 5/1993 | Knoepfler |
| 5,211,649 A | 5/1993 | Kohler et al. |
| 5,221,036 A | 6/1993 | Takase |
| 5,222,975 A | 6/1993 | Crainich |
| 5,246,443 A | 9/1993 | Mai |
| 5,258,009 A | 11/1993 | Conners |
| 5,282,806 A | 2/1994 | Haber et al. |
| 5,282,829 A | 2/1994 | Hermes |
| 5,304,204 A | 4/1994 | Bregen |
| 5,314,424 A | 5/1994 | Nicholas |
| 5,333,422 A | 8/1994 | Warren et al. |
| 5,341,724 A | 8/1994 | Vatel |
| 5,342,395 A | 8/1994 | Jarrett et al. |
| 5,342,396 A | 8/1994 | Cook |
| 5,350,400 A | 9/1994 | Esposito et al. |
| 5,352,235 A | 10/1994 | Koros et al. |
| 5,352,238 A | 10/1994 | Green et al. |
| 5,358,510 A | 10/1994 | Luscombe et al. |
| 5,366,479 A | 11/1994 | McGarry et al. |
| 5,379,933 A | 1/1995 | Green et al. |
| 5,383,880 A | 1/1995 | Hooven |
| 5,383,888 A | 1/1995 | Zvenyatsky et al. |
| 5,383,895 A | 1/1995 | Holmes et al. |
| 5,389,098 A | 2/1995 | Tsuruta et al. |
| 5,397,324 A | 3/1995 | Carroll et al. |
| 5,405,344 A | 4/1995 | Williamson et al. |
| 5,415,334 A | 5/1995 | Williamson, IV et al. |
| 5,417,361 A | 5/1995 | Williamson, IV |
| 5,425,745 A | 6/1995 | Green et al. |
| 5,449,365 A | 9/1995 | Green et al. |
| 5,456,401 A | 10/1995 | Green et al. |
| 5,474,566 A | 12/1995 | Alesi et al. |
| 5,478,354 A | 12/1995 | Tovey et al. |
| 5,480,089 A | 1/1996 | Blewett |
| 5,482,197 A | 1/1996 | Green et al. |
| 5,484,095 A | 1/1996 | Green et al. |
| 5,484,451 A | 1/1996 | Akopov et al. |
| 5,485,947 A | 1/1996 | Olson et al. |
| 5,485,952 A | 1/1996 | Fontayne |
| 5,487,499 A | 1/1996 | Sorrentino et al. |
| 5,487,500 A | 1/1996 | Knodel et al. |
| 5,489,058 A | 2/1996 | Plyley et al. |
| 5,497,933 A | 3/1996 | DeFonzo et al. |
| 5,503,320 A | 4/1996 | Webster et al. |
| 5,503,638 A | 4/1996 | Cooper et al. |
| 5,509,596 A | 4/1996 | Green et al. |
| 5,529,235 A | 6/1996 | Boiarski et al. |
| 5,533,521 A | 7/1996 | Granger |
| 5,535,934 A | 7/1996 | Boiarski et al. |
| 5,535,935 A | 7/1996 | Vidal et al. |
| 5,535,937 A | 7/1996 | Boiarski et al. |
| 5,540,375 A | 7/1996 | Bolanos et al. |
| 5,542,594 A | 8/1996 | McKean et al. |
| 5,547,117 A | 8/1996 | Hamblin et al. |
| 5,549,628 A | 8/1996 | Cooper et al. |
| 5,553,765 A | 9/1996 | Knodel et al. |
| 5,554,169 A | 9/1996 | Green et al. |
| 5,558,665 A | 9/1996 | Kieturakis |
| 5,560,530 A | 10/1996 | Bolanos et al. |
| 5,560,532 A | 10/1996 | DeFonzo et al. |
| 5,562,239 A | 10/1996 | Boiarski et al. |
| 5,562,241 A | 10/1996 | Knodel et al. |
| 5,562,682 A | 10/1996 | Oberlin et al. |
| 5,564,615 A | 10/1996 | Bishop et al. |
| 5,571,116 A | 11/1996 | Bolanos et al. |
| 5,575,799 A | 11/1996 | Bolanos et al. |
| 5,575,803 A | 11/1996 | Cooper et al. |
| 5,577,654 A | 11/1996 | Bishop |
| 5,579,978 A | 12/1996 | Green et al. |
| 5,580,067 A | 12/1996 | Hamblin et al. |
| 5,582,611 A | 12/1996 | Tsuruta et al. |
| 5,584,425 A | 12/1996 | Savage et al. |
| 5,586,711 A | 12/1996 | Plyley et al. |
| 5,588,579 A | 12/1996 | Schnut et al. |
| 5,588,580 A | 12/1996 | Paul et al. |
| 5,588,581 A | 12/1996 | Conlon et al. |
| 5,597,107 A | 1/1997 | Knodel et al. |
| 5,601,224 A | 2/1997 | Bishop et al. |
| 5,603,443 A | 2/1997 | Clark et al. |
| 5,605,272 A | 2/1997 | Witt et al. |
| 5,605,273 A | 2/1997 | Hamblin et al. |
| 5,607,094 A | 3/1997 | Clark et al. |
| 5,607,095 A | 3/1997 | Smith et al. |
| 5,609,285 A | 3/1997 | Grant et al. |
| 5,624,452 A | 4/1997 | Yates |
| 5,628,446 A | 5/1997 | Geiste et al. |
| 5,630,539 A | 5/1997 | Plyley et al. |
| 5,630,540 A | 5/1997 | Blewett |
| 5,632,432 A | 5/1997 | Schulze et al. |
| 5,632,433 A | 5/1997 | Grant et al. |
| 5,634,584 A | 6/1997 | Okorocha et al. |
| 5,636,779 A | 6/1997 | Palmer |
| 5,636,780 A | 6/1997 | Green et al. |
| 5,639,008 A | 6/1997 | Gallagher et al. |
| 5,645,209 A | 7/1997 | Green et al. |
| 5,647,526 A | 7/1997 | Green et al. |
| 5,649,937 A | 7/1997 | Bito et al. |
| 5,651,491 A | 7/1997 | Heaton et al. |

| Patent No. | Date | Inventor |
|---|---|---|
| 5,653,373 A | 8/1997 | Green et al. |
| 5,653,374 A | 8/1997 | Young et al. |
| 5,655,698 A | 8/1997 | Yoon |
| 5,657,921 A | 8/1997 | Young et al. |
| 5,662,258 A | 9/1997 | Knodel et al. |
| 5,662,260 A | 9/1997 | Yoon |
| 5,667,527 A | 9/1997 | Cook |
| 5,669,544 A | 9/1997 | Schulze et al. |
| 5,673,840 A | 10/1997 | Schulze et al. |
| 5,673,841 A | 10/1997 | Schulze et al. |
| 5,673,842 A | 10/1997 | Bittner et al. |
| 5,678,748 A | 10/1997 | Plyley et al. |
| 5,680,981 A | 10/1997 | Mililli et al. |
| 5,680,982 A | 10/1997 | Schulze et al. |
| 5,680,983 A | 10/1997 | Plyley et al. |
| 5,685,474 A | 11/1997 | Seeber |
| 5,688,270 A | 11/1997 | Yates et al. |
| 5,690,269 A | 11/1997 | Bolanos et al. |
| 5,692,668 A | 12/1997 | Schulze et al. |
| 5,697,543 A | 12/1997 | Burdorff |
| 5,700,270 A | 12/1997 | Peyser et al. |
| 5,702,408 A | 12/1997 | Wales et al. |
| 5,704,534 A | 1/1998 | Huitema et al. |
| 5,706,997 A | 1/1998 | Green et al. |
| 5,706,998 A | 1/1998 | Plyley et al. |
| 5,709,334 A | 1/1998 | Sorrentino et al. |
| 5,711,472 A | 1/1998 | Bryan |
| 5,713,505 A | 2/1998 | Huitema |
| 5,715,987 A | 2/1998 | Kelley et al. |
| 5,715,988 A | 2/1998 | Palmer |
| 5,716,366 A | 2/1998 | Yates |
| 5,718,359 A | 2/1998 | Palmer et al. |
| 5,725,536 A | 3/1998 | Oberlin et al. |
| 5,725,554 A | 3/1998 | Simon et al. |
| 5,728,121 A | 3/1998 | Bimbo et al. |
| 5,730,758 A | 3/1998 | Allgeyer |
| 5,732,871 A | 3/1998 | Clark et al. |
| 5,732,872 A | 3/1998 | Bolduc et al. |
| 5,735,445 A | 4/1998 | Vidal et al. |
| 5,735,874 A | 4/1998 | Measamer et al. |
| 5,743,456 A | 4/1998 | Jones et al. |
| 5,752,644 A | 5/1998 | Bolanos et al. |
| 5,758,814 A | 6/1998 | Gallagher et al. |
| 5,762,255 A | 6/1998 | Chrisman et al. |
| 5,762,256 A | 6/1998 | Mastri et al. |
| 5,779,130 A | 7/1998 | Alesi et al. |
| 5,779,132 A | 7/1998 | Knodel et al. |
| 5,782,396 A | 7/1998 | Mastri et al. |
| 5,782,397 A | 7/1998 | Koukline |
| 5,785,232 A | 7/1998 | Vidal et al. |
| 5,794,834 A | 8/1998 | Hamblin et al. |
| 5,797,536 A | 8/1998 | Smith et al. |
| 5,797,537 A | 8/1998 | Oberlin et al. |
| 5,797,538 A | 8/1998 | Heaton et al. |
| 5,799,857 A | 9/1998 | Robertson et al. |
| 5,820,009 A | 10/1998 | Melling et al. |
| 5,826,776 A | 10/1998 | Schulze et al. |
| 5,829,662 A | 11/1998 | Allen et al. |
| 5,833,690 A | 11/1998 | Yates et al. |
| 5,833,695 A | 11/1998 | Yoon |
| 5,836,503 A | 11/1998 | Ehrenfels et al. |
| 5,839,639 A | 11/1998 | Sauer et al. |
| 5,855,311 A | 1/1999 | Hamblin et al. |
| 5,865,361 A | 2/1999 | Milliman et al. |
| 5,868,760 A | 2/1999 | McGuckin, Jr. |
| 5,871,135 A | 2/1999 | Williamson, IV et al. |
| 5,876,401 A | 3/1999 | Schulze et al. |
| 5,878,937 A | 3/1999 | Green et al. |
| 5,878,938 A | 3/1999 | Bittner et al. |
| 5,893,506 A | 4/1999 | Powell |
| 5,894,979 A | 4/1999 | Powell |
| 5,897,562 A | 4/1999 | Bolanos et al. |
| 5,901,895 A | 5/1999 | Heaton et al. |
| 5,906,625 A | 5/1999 | Bito et al. |
| 5,908,427 A | 6/1999 | McKean et al. |
| 5,911,353 A | 6/1999 | Bolanos et al. |
| 5,915,616 A | 6/1999 | Viola et al. |
| 5,918,791 A | 7/1999 | Sorrentino et al. |
| 5,919,198 A | 7/1999 | Graves, Jr. et al. |
| 5,938,667 A | 8/1999 | Peyser et al. |
| 5,941,442 A | 8/1999 | Geiste et al. |
| 5,951,552 A | 9/1999 | Long et al. |
| 5,951,574 A | 9/1999 | Stefanchik et al. |
| 5,954,259 A | 9/1999 | Viola et al. |
| 5,988,479 A | 11/1999 | Palmer |
| 6,010,054 A | 1/2000 | Johnson et al. |
| 6,032,849 A | 3/2000 | Mastri et al. |
| 6,033,427 A | 3/2000 | Lee |
| 6,045,560 A | 4/2000 | McKean et al. |
| 6,050,472 A | 4/2000 | Shibata |
| 6,079,606 A | 6/2000 | Milliman et al. |
| 6,083,242 A | 7/2000 | Cook |
| 6,086,600 A | 7/2000 | Kortenbach |
| 6,099,551 A | 8/2000 | Gabbay |
| 6,102,271 A | 8/2000 | Longo et al. |
| 6,109,500 A | 8/2000 | Alli et al. |
| 6,117,158 A | 9/2000 | Measamer et al. |
| 6,119,913 A | 9/2000 | Adams et al. |
| 6,126,058 A | 10/2000 | Adams et al. |
| 6,131,789 A | 10/2000 | Schulze et al. |
| 6,155,473 A | 12/2000 | Tompkins et al. |
| 6,156,056 A | 12/2000 | Kearns et al. |
| 6,162,208 A | 12/2000 | Hipps |
| 6,168,605 B1 | 1/2001 | Measamer et al. |
| 6,171,330 B1 | 1/2001 | Benchetrit |
| 6,202,914 B1 | 3/2001 | Geiste et al. |
| 6,228,084 B1 | 5/2001 | Kirwan, Jr. |
| 6,241,139 B1 | 6/2001 | Milliman et al. |
| 6,250,532 B1 | 6/2001 | Green et al. |
| 6,264,086 B1 | 7/2001 | McGuckin, Jr. |
| 6,264,087 B1 | 7/2001 | Whitman |
| 6,273,897 B1 | 8/2001 | Dalessandro et al. |
| 6,302,311 B1 | 10/2001 | Adams et al. |
| 6,315,184 B1 | 11/2001 | Whitman |
| 6,325,810 B1 | 12/2001 | Hamilton et al. |
| 6,330,965 B1 | 12/2001 | Milliman et al. |
| 6,387,113 B1 | 5/2002 | Hawkins et al. |
| 6,387,114 B2 | 5/2002 | Adams |
| 6,406,440 B1 | 6/2002 | Stefanchik |
| RE37,814 E | 8/2002 | Allgeyer |
| 6,436,107 B1 | 8/2002 | Wang et al. |
| 6,443,973 B1 | 9/2002 | Whitman |
| 6,482,200 B2 | 11/2002 | Shippert |
| 6,488,197 B1 | 12/2002 | Whitman |
| 6,491,201 B1 | 12/2002 | Whitman |
| 6,494,896 B1 | 12/2002 | D'Alessio et al. |
| 6,503,257 B2 | 1/2003 | Grant et al. |
| 6,505,768 B2 | 1/2003 | Whitman |
| 6,517,565 B1 | 2/2003 | Whitman et al. |
| 6,569,171 B2 | 5/2003 | DeGuillebon et al. |
| 6,578,751 B2 | 6/2003 | Hartwick |
| 6,588,643 B2 | 7/2003 | Bolduc et al. |
| 6,592,597 B2 | 7/2003 | Grant et al. |
| 6,601,749 B2 | 8/2003 | Sullivan et al. |
| 6,602,252 B2 | 8/2003 | Mollenauer |
| 6,616,686 B2 | 9/2003 | Coleman et al. |
| 6,619,529 B2 | 9/2003 | Green et al. |
| 6,620,166 B1 | 9/2003 | Wenstrom, Jr. et al. |
| 6,629,988 B2 | 10/2003 | Weadock |
| 6,644,532 B2 | 11/2003 | Green et al. |
| 6,656,193 B2 | 12/2003 | Grant et al. |
| 6,669,073 B2 | 12/2003 | Milliman et al. |
| 6,681,978 B2 | 1/2004 | Geiste et al. |
| 6,681,979 B2 | 1/2004 | Whitman |
| 6,682,528 B2 | 1/2004 | Frazier et al. |
| 6,695,199 B2 | 2/2004 | Whitman |

| Patent No. | Date | Inventor(s) |
|---|---|---|
| 6,698,643 B2 | 3/2004 | Whitman |
| 6,716,233 B1 | 4/2004 | Whitman |
| 6,723,087 B2 | 4/2004 | O'Neill et al. |
| 6,752,768 B2 | 6/2004 | Burdorff et al. |
| 6,755,338 B2 | 6/2004 | Hahnen et al. |
| 6,767,356 B2 | 7/2004 | Kanner et al. |
| 6,773,438 B1 | 8/2004 | Knodel et al. |
| 6,786,382 B1 | 9/2004 | Hoffman |
| 6,786,896 B1 | 9/2004 | Madani et al. |
| 6,793,652 B1 | 9/2004 | Whitman et al. |
| 6,805,273 B2 | 10/2004 | Bilotti et al. |
| 6,814,741 B2 | 11/2004 | Bowman et al. |
| 6,817,508 B1 | 11/2004 | Racenet et al. |
| 6,817,509 B2 | 11/2004 | Geiste et al. |
| 6,821,273 B2 | 11/2004 | Mollenauer |
| 6,830,174 B2 | 12/2004 | Hillstead et al. |
| 6,835,199 B2 | 12/2004 | McGuckin, Jr. et al. |
| 6,843,403 B2 | 1/2005 | Whitman |
| 6,846,307 B2 | 1/2005 | Whitman et al. |
| 6,846,308 B2 | 1/2005 | Whitman et al. |
| 6,846,309 B2 | 1/2005 | Whitman et al. |
| 6,849,071 B2 | 2/2005 | Whitman et al. |
| RE38,708 E | 3/2005 | Bolanos et al. |
| 6,877,647 B2 | 4/2005 | Green et al. |
| 6,905,057 B2 | 6/2005 | Swayze et al. |
| 6,945,444 B2 | 9/2005 | Gresham et al. |
| 6,953,138 B1 | 10/2005 | Dworak et al. |
| 6,953,139 B2 | 10/2005 | Milliman et al. |
| 6,959,852 B2 | 11/2005 | Shelton, IV et al. |
| 6,964,363 B2 | 11/2005 | Wales et al. |
| 6,978,921 B2 | 12/2005 | Shelton, IV et al. |
| 6,978,922 B2 | 12/2005 | Bilotti et al. |
| 6,981,628 B2 | 1/2006 | Wales |
| 6,986,451 B1 | 1/2006 | Mastri et al. |
| 6,988,649 B2 | 1/2006 | Shelton, IV et al. |
| 6,988,650 B2 | 1/2006 | Schwemberger et al. |
| 7,000,818 B2 | 2/2006 | Shelton, IV et al. |
| 7,000,819 B2 | 2/2006 | Swayze et al. |
| 7,008,435 B2 | 3/2006 | Cummins |
| 7,032,798 B2 | 4/2006 | Whitman et al. |
| 7,032,799 B2 | 4/2006 | Viola et al. |
| 7,044,352 B2 | 5/2006 | Shelton, IV et al. |
| 7,044,353 B2 | 5/2006 | Mastri et al. |
| 7,048,687 B1 | 5/2006 | Reuss et al. |
| 7,055,730 B2 | 6/2006 | Ehrenfels et al. |
| 7,055,731 B2 | 6/2006 | Shelton, IV et al. |
| 7,056,330 B2 | 6/2006 | Gayton |
| 7,059,508 B2 | 6/2006 | Shelton, IV et al. |
| 7,070,083 B2 | 7/2006 | Jankowski |
| 7,077,856 B2 | 7/2006 | Whitman |
| 7,080,769 B2 | 7/2006 | Vresh et al. |
| 7,081,114 B2 | 7/2006 | Rashidi |
| 7,083,075 B2 | 8/2006 | Swayze et al. |
| 7,090,673 B2 | 8/2006 | Dycus et al. |
| 7,090,684 B2 | 8/2006 | McGuckin, Jr. et al. |
| 7,097,089 B2 | 8/2006 | Marczyk |
| 7,108,695 B2 | 9/2006 | Witt et al. |
| 7,108,709 B2 | 9/2006 | Cummins |
| 7,111,769 B2 | 9/2006 | Wales et al. |
| 7,112,214 B2 | 9/2006 | Peterson et al. |
| 7,114,642 B2 | 10/2006 | Whitman |
| 7,118,582 B1 | 10/2006 | Wang et al. |
| 7,121,446 B2 | 10/2006 | Arad et al. |
| 7,122,028 B2 | 10/2006 | Looper et al. |
| 7,128,253 B2 | 10/2006 | Mastri et al. |
| 7,128,254 B2 | 10/2006 | Shelton, IV et al. |
| 7,140,527 B2 | 11/2006 | Ehrenfels et al. |
| 7,140,528 B2 | 11/2006 | Shelton, IV |
| 7,143,923 B2 | 12/2006 | Shelton, IV et al. |
| 7,143,924 B2 | 12/2006 | Scirica et al. |
| 7,143,925 B2 | 12/2006 | Shelton, IV et al. |
| 7,143,926 B2 | 12/2006 | Shelton, IV |
| 7,147,138 B2 | 12/2006 | Shelton, IV |
| 7,159,750 B2 | 1/2007 | Racenet et al. |
| 7,160,299 B2 | 1/2007 | Baily |
| 7,168,604 B2 | 1/2007 | Milliman et al. |
| 7,172,104 B2 | 2/2007 | Scirica et al. |
| 7,188,758 B2 | 3/2007 | Viola et al. |
| 7,207,471 B2 | 4/2007 | Heinrich et al. |
| 7,207,472 B2 | 4/2007 | Wukusick et al. |
| 7,210,609 B2 | 5/2007 | Leiboff et al. |
| 7,213,736 B2 | 5/2007 | Wales et al. |
| 7,220,272 B2 | 5/2007 | Weadock |
| 7,225,964 B2 | 6/2007 | Mastri et al. |
| 7,235,089 B1 | 6/2007 | McGuckin, Jr. |
| 7,238,195 B2 | 7/2007 | Viola |
| 7,241,288 B2 | 7/2007 | Braun |
| 7,246,734 B2 | 7/2007 | Shelton, IV |
| 7,258,262 B2 | 8/2007 | Mastri et al. |
| 7,278,563 B1 | 10/2007 | Green |
| 7,296,724 B2 | 11/2007 | Green et al. |
| 7,297,149 B2 | 11/2007 | Vitali et al. |
| 7,303,106 B2 | 12/2007 | Milliman et al. |
| 7,303,107 B2 | 12/2007 | Milliman et al. |
| 7,303,108 B2 | 12/2007 | Shelton, IV |
| 7,328,828 B2 | 2/2008 | Ortiz et al. |
| 7,328,829 B2 | 2/2008 | Arad et al. |
| 7,343,920 B2 | 3/2008 | Toby et al. |
| 7,354,447 B2 | 4/2008 | Shelton, IV et al. |
| 7,364,061 B2 | 4/2008 | Swayze et al. |
| 7,380,695 B2 | 6/2008 | Doll et al. |
| 7,380,696 B2 | 6/2008 | Shelton, IV et al. |
| 7,396,356 B2 | 7/2008 | Mollenauer |
| 7,398,907 B2 | 7/2008 | Racenet et al. |
| 7,398,908 B2 | 7/2008 | Holsten et al. |
| 7,404,508 B2 | 7/2008 | Smith et al. |
| 7,404,509 B2 | 7/2008 | Ortiz et al. |
| 7,407,075 B2 | 8/2008 | Holsten et al. |
| 7,407,078 B2 | 8/2008 | Shelton, IV et al. |
| 7,410,086 B2 | 8/2008 | Ortiz et al. |
| 7,416,101 B2 | 8/2008 | Shelton, IV et al. |
| 7,422,136 B1 | 9/2008 | Marczyk |
| 7,422,139 B2 | 9/2008 | Shelton, IV et al. |
| 7,424,965 B2 | 9/2008 | Racenet et al. |
| 7,431,188 B1 | 10/2008 | Marczyk |
| 7,431,189 B2 | 10/2008 | Shelton, IV et al. |
| 7,431,730 B2 | 10/2008 | Viola |
| 7,434,715 B2 | 10/2008 | Shelton, IV et al. |
| 7,434,717 B2 | 10/2008 | Shelton, IV et al. |
| 7,438,209 B1 | 10/2008 | Hess et al. |
| 7,441,684 B2 | 10/2008 | Shelton, IV et al. |
| 7,441,685 B1 | 10/2008 | Boudreaux |
| 7,448,525 B2 | 11/2008 | Shelton, IV et al. |
| 7,464,846 B2 | 12/2008 | Shelton, IV et al. |
| 7,464,847 B2 * | 12/2008 | Viola et al. ............... 227/175.2 |
| 7,464,849 B2 | 12/2008 | Shelton, IV et al. |
| 7,467,740 B2 | 12/2008 | Shelton, IV et al. |
| 7,472,815 B2 | 1/2009 | Shelton, IV et al. |
| 7,490,749 B2 | 2/2009 | Schall et al. |
| 7,494,039 B2 | 2/2009 | Racenet et al. |
| 7,500,979 B2 | 3/2009 | Hueil et al. |
| 7,506,790 B2 | 3/2009 | Shelton, IV |
| 7,510,107 B2 | 3/2009 | Timm et al. |
| 7,546,940 B2 | 6/2009 | Milliman et al. |
| 7,665,646 B2 | 2/2010 | Prommersberger |
| 2002/0117534 A1 | 8/2002 | Green et al. |
| 2002/0165541 A1 | 11/2002 | Whitman |
| 2004/0006372 A1 | 1/2004 | Racenet et al. |
| 2004/0034369 A1 | 2/2004 | Sauer et al. |
| 2004/0044360 A1 | 3/2004 | Lowe |
| 2004/0094597 A1 | 5/2004 | Whitman et al. |
| 2004/0108357 A1 | 6/2004 | Milliman et al. |
| 2004/0111081 A1 | 6/2004 | Whitman et al. |
| 2004/0164123 A1 | 8/2004 | Racenet et al. |
| 2004/0167572 A1 | 8/2004 | Roth et al. |
| 2004/0173659 A1 | 9/2004 | Green et al. |

| | | |
|---|---|---|
| 2004/0222268 A1 | 11/2004 | Bilotti et al. |
| 2004/0232201 A1 | 11/2004 | Wenchell et al. |
| 2004/0243151 A1 | 12/2004 | Demmy et al. |
| 2004/0243176 A1 | 12/2004 | Hahnen et al. |
| 2004/0254608 A1 | 12/2004 | Huitema et al. |
| 2005/0054946 A1 | 3/2005 | Krzyzanowski |
| 2005/0059997 A1 | 3/2005 | Bauman et al. |
| 2005/0080454 A1 | 4/2005 | Drews et al. |
| 2005/0103819 A1 | 5/2005 | Racenet et al. |
| 2005/0107824 A1 | 5/2005 | Hillstead et al. |
| 2005/0119669 A1 | 6/2005 | Demmy |
| 2005/0125009 A1 | 6/2005 | Perry et al. |
| 2005/0131390 A1 | 6/2005 | Heinrich et al. |
| 2005/0131457 A1 | 6/2005 | Douglas et al. |
| 2005/0143759 A1 | 6/2005 | Kelly |
| 2005/0171522 A1 | 8/2005 | Christopherson |
| 2005/0184121 A1 | 8/2005 | Heinrich |
| 2005/0187576 A1 | 8/2005 | Whitman et al. |
| 2005/0159397 A1 | 9/2005 | Jankowski |
| 2005/0216055 A1 | 9/2005 | Scirica et al. |
| 2005/0256522 A1 | 11/2005 | Francischelli et al. |
| 2005/0263563 A1 | 12/2005 | Racenet et al. |
| 2005/0274768 A1 | 12/2005 | Cummins et al. |
| 2006/0011699 A1 | 1/2006 | Olson et al. |
| 2006/0047303 A1 | 3/2006 | Ortiz et al. |
| 2006/0047307 A1 | 3/2006 | Ortiz et al. |
| 2006/0049229 A1 | 3/2006 | Milliman et al. |
| 2006/0052825 A1 | 3/2006 | Ransick et al. |
| 2006/0060630 A1 | 3/2006 | Shelton, IV et al. |
| 2006/0085031 A1 | 4/2006 | Bettuchi |
| 2006/0085033 A1 | 4/2006 | Criscuolo et al. |
| 2006/0100643 A1 | 5/2006 | Laufer et al. |
| 2006/0108393 A1 | 5/2006 | Heinrich et al. |
| 2006/0122636 A1 | 6/2006 | Bailly et al. |
| 2006/0149163 A1 | 7/2006 | Hibner et al. |
| 2006/0151567 A1 | 7/2006 | Roy |
| 2006/0180634 A1 | 8/2006 | Shelton, IV et al. |
| 2006/0217729 A1 | 9/2006 | Eskridge et al. |
| 2006/0226196 A1 | 10/2006 | Hueil et al. |
| 2006/0241655 A1 | 10/2006 | Viola |
| 2006/0241692 A1 | 10/2006 | McGuckin, Jr. et al. |
| 2006/0273135 A1 | 12/2006 | Beetel |
| 2006/0278680 A1 | 12/2006 | Viola et al. |
| 2006/0278681 A1 | 12/2006 | Viola et al. |
| 2006/0289602 A1 | 12/2006 | Wales et al. |
| 2007/0023476 A1 | 2/2007 | Whitman et al. |
| 2007/0023477 A1 | 2/2007 | Whitman et al. |
| 2007/0027469 A1 | 2/2007 | Smith et al. |
| 2007/0034668 A1 | 2/2007 | Holsten et al. |
| 2007/0045379 A1 | 3/2007 | Shelton, IV |
| 2007/0055219 A1 | 3/2007 | Whitman et al. |
| 2007/0073340 A1 | 3/2007 | Shelton, IV et al. |
| 2007/0083234 A1 | 4/2007 | Shelton, IV et al. |
| 2007/0084897 A1 | 4/2007 | Shelton, IV et al. |
| 2007/0102452 A1 | 5/2007 | Shelton, IV et al. |
| 2007/0102453 A1 | 5/2007 | Morgan et al. |
| 2007/0102472 A1 | 5/2007 | Shelton, IV |
| 2007/0102473 A1 | 5/2007 | Shelton, IV et al. |
| 2007/0102474 A1 | 5/2007 | Shelton, IV et al. |
| 2007/0106317 A1 | 5/2007 | Shelton, IV et al. |
| 2007/0114261 A1 | 5/2007 | Ortiz et al. |
| 2007/0158385 A1 | 7/2007 | Hueil et al. |
| 2007/0170225 A1 | 7/2007 | Shelton, IV et al. |
| 2007/0175949 A1 | 8/2007 | Shelton, IV et al. |
| 2007/0175950 A1 | 8/2007 | Shelton, IV et al. |
| 2007/0175951 A1 | 8/2007 | Shelton, IV et al. |
| 2007/0175953 A1 | 8/2007 | Shelton, IV et al. |
| 2007/0175955 A1 | 8/2007 | Shelton, IV et al. |
| 2007/0175956 A1 | 8/2007 | Swayze et al. |
| 2007/0175957 A1 | 8/2007 | Shelton, IV et al. |
| 2007/0175958 A1 | 8/2007 | Shelton, IV et al. |
| 2007/0175959 A1 | 8/2007 | Shelton, IV et al. |
| 2007/0175960 A1 | 8/2007 | Shelton, IV et al. |
| 2007/0175961 A1 | 8/2007 | Shelton, IV et al. |
| 2007/0175964 A1 | 8/2007 | Shelton, IV et al. |
| 2007/0179476 A1 | 8/2007 | Shelton, IV et al. |
| 2007/0181632 A1 | 8/2007 | Milliman |
| 2007/0194079 A1 | 8/2007 | Hueil et al. |
| 2007/0194080 A1 | 8/2007 | Swayze et al. |
| 2007/0194081 A1 | 8/2007 | Hueil et al. |
| 2007/0194082 A1 | 8/2007 | Morgan et al. |
| 2007/0233053 A1 | 10/2007 | Shelton, IV et al. |
| 2007/0246505 A1 | 10/2007 | Pace-Floridia et al. |
| 2007/0262116 A1 | 11/2007 | Hueil et al. |
| 2007/0295780 A1 | 12/2007 | Shelton et al. |
| 2008/0029570 A1 | 2/2008 | Shelton et al. |
| 2008/0029571 A1 | 2/2008 | Shelton et al. |
| 2008/0029572 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0029576 A1 | 2/2008 | Shelton et al. |
| 2008/0029577 A1 | 2/2008 | Shelton et al. |
| 2008/0035701 A1 | 2/2008 | Racenet et al. |
| 2008/0041916 A1 | 2/2008 | Milliman et al. |
| 2008/0041917 A1 | 2/2008 | Racenet et al. |
| 2008/0078800 A1 | 4/2008 | Hess et al. |
| 2008/0078801 A1 | 4/2008 | Shelton et al. |
| 2008/0078802 A1 | 4/2008 | Hess et al. |
| 2008/0078803 A1 | 4/2008 | Shelton et al. |
| 2008/0078804 A1 | 4/2008 | Shelton et al. |
| 2008/0078805 A1 | 4/2008 | Omaits et al. |
| 2008/0078806 A1 | 4/2008 | Omaits et al. |
| 2008/0078807 A1 | 4/2008 | Hess et al. |
| 2008/0078808 A1 | 4/2008 | Hess et al. |
| 2008/0082115 A1 | 4/2008 | Morgan et al. |
| 2008/0082124 A1 | 4/2008 | Hess et al. |
| 2008/0082125 A1 | 4/2008 | Murray et al. |
| 2008/0082126 A1 | 4/2008 | Murray et al. |
| 2008/0083813 A1 | 4/2008 | Zemlok et al. |
| 2008/0140115 A1 | 6/2008 | Stopek |
| 2008/0164296 A1 | 7/2008 | Shelton et al. |
| 2008/0167522 A1 | 7/2008 | Giordano et al. |
| 2008/0167644 A1 | 7/2008 | Shelton et al. |
| 2008/0167670 A1 | 7/2008 | Shelton et al. |
| 2008/0167671 A1 | 7/2008 | Giordano et al. |
| 2008/0167672 A1 | 7/2008 | Giordano et al. |
| 2008/0167736 A1 | 7/2008 | Swayze et al. |
| 2008/0169327 A1 | 7/2008 | Shelton et al. |
| 2008/0169328 A1 | 7/2008 | Shelton |
| 2008/0169329 A1 | 7/2008 | Shelton et al. |
| 2008/0169330 A1 | 7/2008 | Shelton et al. |
| 2008/0169331 A1 | 7/2008 | Shelton et al. |
| 2008/0169332 A1 | 7/2008 | Shelton et al. |
| 2008/0169333 A1 | 7/2008 | Shelton et al. |
| 2008/0197167 A1 | 8/2008 | Viola et al. |
| 2008/0210738 A1 | 9/2008 | Shelton et al. |
| 2008/0237296 A1 | 10/2008 | Boudreaux et al. |
| 2008/0251568 A1 | 10/2008 | Zemlok et al. |
| 2008/0290134 A1 | 11/2008 | Bettuchi et al. |
| 2008/0296343 A1 | 12/2008 | Schall et al. |
| 2008/0296345 A1 | 12/2008 | Shelton, IV et al. |
| 2008/0296346 A1 | 12/2008 | Shelton, IV et al. |
| 2008/0296347 A1 | 12/2008 | Shelton, IV et al. |
| 2008/0300579 A1 | 12/2008 | Broehl et al. |
| 2008/0300580 A1 | 12/2008 | Shelton, IV et al. |
| 2008/0300613 A1 | 12/2008 | Shelton, IV et al. |
| 2008/0308601 A1 | 12/2008 | Timm et al. |
| 2008/0308602 A1 | 12/2008 | Timm et al. |
| 2008/0308603 A1 | 12/2008 | Shelton, IV et al. |
| 2008/0308606 A1 | 12/2008 | Timm et al. |
| 2008/0308607 A1 | 12/2008 | Timm et al. |
| 2008/0308608 A1 | 12/2008 | Prommersberger |
| 2008/0314954 A1 | 12/2008 | Boudreaux |
| 2008/0314955 A1 | 12/2008 | Boudreaux et al. |
| 2008/0314956 A1 | 12/2008 | Boudreaux |

| | | | | | | |
|---|---|---|---|---|---|---|
| 2008/0314957 A1 | 12/2008 | Boudreaux | EP | 0276104 A2 | 7/1988 |
| 2008/0314960 A1 | 12/2008 | Marczyk et al. | EP | 0639349 A2 | 2/1994 |
| 2008/0314961 A1 | 12/2008 | Boudreaux et al. | EP | 0324636 B1 | 3/1994 |
| 2008/0314962 A1 | 12/2008 | Boudreaux | EP | 0593920 A1 | 4/1994 |
| 2009/0001121 A1 | 1/2009 | Hess et al. | EP | 0600182 A2 | 6/1994 |
| 2009/0001122 A1 | 1/2009 | Prommersberger et al. | EP | 0630612 A1 | 12/1994 |
| 2009/0001123 A1 | 1/2009 | Morgan et al. | EP | 0634144 A1 | 1/1995 |
| 2009/0001124 A1 | 1/2009 | Hess et al. | EP | 0646356 A2 | 4/1995 |
| 2009/0001125 A1 | 1/2009 | Hess et al. | EP | 0646357 A1 | 4/1995 |
| 2009/0001126 A1 | 1/2009 | Hess et al. | EP | 0653189 A2 | 5/1995 |
| 2009/0001128 A1 | 1/2009 | Weisenburgh, II et al. | EP | 0669104 A1 | 8/1995 |
| 2009/0001130 A1 | 1/2009 | Hess et al. | EP | 0511470 B1 | 10/1995 |
| 2009/0005807 A1 | 1/2009 | Hess et al. | EP | 0679367 A2 | 11/1995 |
| 2009/0005808 A1 | 1/2009 | Hess et al. | EP | 0392547 B1 | 12/1995 |
| 2009/0005809 A1 | 1/2009 | Hess et al. | EP | 0685204 A1 | 12/1995 |
| 2009/0012556 A1 | 1/2009 | Boudreaux et al. | EP | 0699418 A1 | 3/1996 |
| 2009/0020613 A1 | 1/2009 | Chang et al. | EP | 0702937 A1 | 3/1996 |
| 2009/0020614 A1 | 1/2009 | Gelbman | EP | 0705571 A1 | 4/1996 |
| 2009/0076534 A1 | 3/2009 | Shelton, IV et al. | EP | 0484677 B2 | 6/1996 |
| 2009/0090763 A1 | 4/2009 | Zemlok et al. | EP | 0541987 B1 | 7/1996 |
| 2009/0200355 A1 | 8/2009 | Baxter, III et al. | EP | 0667119 B1 | 7/1996 |
| 2009/0206123 A1 | 8/2009 | Doll et al. | EP | 0770355 A1 | 5/1997 |
| 2009/0206124 A1 | 8/2009 | Hall et al. | EP | 0503662 B1 | 6/1997 |
| 2009/0206125 A1 | 8/2009 | Huitema et al. | EP | 0578425 B1 | 9/1997 |
| 2009/0206126 A1 | 8/2009 | Huitema et al. | EP | 0625335 B1 | 11/1997 |
| 2009/0206128 A1 | 8/2009 | Hueil et al. | EP | 0552423 B1 | 1/1998 |
| 2009/0206129 A1 | 8/2009 | Doll et al. | EP | 0592244 B1 | 1/1998 |
| 2009/0206130 A1 | 8/2009 | Hall et al. | EP | 0648476 B1 | 1/1998 |
| 2009/0206131 A1 | 8/2009 | Weisenburgh, II et al. | EP | 0676173 B1 | 9/1998 |
| 2009/0206132 A1 | 8/2009 | Hueil et al. | EP | 0603472 B1 | 11/1998 |
| 2009/0206133 A1 | 8/2009 | Morgan et al. | EP | 0605351 B1 | 11/1998 |
| 2009/0206134 A1 | 8/2009 | Swayze et al. | EP | 0878169 A1 | 11/1998 |
| 2009/0206137 A1 | 8/2009 | Hall et al. | EP | 0879742 A1 | 11/1998 |
| 2009/0206138 A1 | 8/2009 | Smith et al. | EP | 0760230 B1 | 2/1999 |
| 2009/0206139 A1 | 8/2009 | Hall et al. | EP | 0537572 B1 | 6/1999 |
| 2009/0206140 A1 | 8/2009 | Scheib et al. | EP | 0552050 B1 | 5/2000 |
| 2009/0206142 A1 | 8/2009 | Huitema et al. | EP | 1090592 A1 | 4/2001 |
| 2009/0206143 A1 | 8/2009 | Huitema et al. | EP | 1256318 B1 | 5/2001 |
| 2009/0206144 A1 | 8/2009 | Doll et al. | EP | 0908152 B1 | 1/2002 |
| 2009/0209946 A1 | 8/2009 | Swayze et al. | EP | 0872213 B1 | 5/2002 |
| 2009/0218384 A1 | 9/2009 | Aranyi | EP | 1238634 A2 | 9/2002 |
| 2009/0255974 A1 | 10/2009 | Viola | EP | 0656188 B1 | 1/2003 |
| 2009/0255975 A1 | 10/2009 | Zemlok et al. | EP | 0829235 B1 | 6/2003 |
| 2009/0255976 A1 | 10/2009 | Marczyk et al. | EP | 0813843 B1 | 10/2003 |
| 2009/0255977 A1 | 10/2009 | Zemlok | EP | 0741996 B1 | 2/2004 |
| 2009/0255978 A1 | 10/2009 | Viola et al. | EP | 0705570 B1 | 4/2004 |
| 2009/0289096 A1 | 11/2009 | Shelton, IV et al. | EP | 1086713 B1 | 5/2004 |
| 2010/0032470 A1 | 2/2010 | Hess et al. | EP | 1426012 A1 | 6/2004 |
| 2010/0065605 A1 | 3/2010 | Shelton, IV et al. | EP | 0888749 B1 | 9/2004 |
| 2010/0065609 A1 | 3/2010 | Schwemberger | EP | 1477119 A1 | 11/2004 |
| 2010/0069942 A1 | 3/2010 | Shelton, IV | EP | 1479345 A1 | 11/2004 |
| 2010/0072251 A1 | 3/2010 | Baxter, III et al. | EP | 1479347 A1 | 11/2004 |
| 2010/0072252 A1 | 3/2010 | Baxter, III et al. | EP | 1479348 A1 | 11/2004 |
| 2010/0072253 A1 | 3/2010 | Baxter, III et al. | EP | 1520521 A1 | 4/2005 |
| 2010/0072256 A1 | 3/2010 | Baxter, III et al. | EP | 1520523 A1 | 4/2005 |
| 2010/0076474 A1 | 3/2010 | Yates et al. | EP | 1520525 A1 | 4/2005 |
| 2010/0076475 A1 | 3/2010 | Yates et al. | EP | 1522264 A1 | 4/2005 |
| | | | EP | 1550408 A1 | 7/2005 |
| | FOREIGN PATENT DOCUMENTS | | EP | 1557129 A1 | 7/2005 |
| | | | EP | 1064883 B1 | 8/2005 |
| CA | 2512960 A1 | 1/2006 | EP | 1157666 B1 | 9/2005 |
| CA | 2514274 A1 | 1/2006 | EP | 1621138 A2 | 2/2006 |
| DE | 273689 C | 5/1914 | EP | 1621139 A2 | 2/2006 |
| DE | 1775926 A | 1/1972 | EP | 1621141 A2 | 2/2006 |
| DE | 9412228 U | 9/1994 | EP | 1621145 A2 | 2/2006 |
| DE | 19924311 A1 | 11/2000 | EP | 1652481 A2 | 5/2006 |
| DE | 69328576 T2 | 1/2001 | EP | 1382303 B1 | 6/2006 |
| DE | 20112837 U1 | 10/2001 | EP | 1045672 B1 | 8/2006 |
| DE | 20121753 U1 | 4/2003 | EP | 1617768 B1 | 8/2006 |
| DE | 10314072 A1 | 10/2004 | EP | 1702567 A2 | 9/2006 |
| EP | 0122046 A1 | 10/1984 | EP | 1129665 B1 | 11/2006 |
| EP | 0070230 B1 | 10/1985 | EP | 1256317 B1 | 12/2006 |
| EP | 0033548 B1 | 5/1986 | EP | 1728473 A1 | 12/2006 |

| | | |
|---|---|---|
| EP | 1728475 A2 | 12/2006 |
| EP | 1479346 B1 | 1/2007 |
| EP | 1484024 B1 | 1/2007 |
| EP | 1754445 A2 | 2/2007 |
| EP | 1759812 A1 | 3/2007 |
| EP | 1769756 A1 | 4/2007 |
| EP | 1769758 A1 | 4/2007 |
| EP | 1785097 A2 | 5/2007 |
| EP | 1790293 A2 | 5/2007 |
| EP | 1300117 B1 | 8/2007 |
| EP | 1813199 A1 | 8/2007 |
| EP | 1813201 A1 | 8/2007 |
| EP | 1813203 A2 | 8/2007 |
| EP | 1813207 A1 | 8/2007 |
| EP | 1813209 A1 | 8/2007 |
| EP | 1872727 A1 | 1/2008 |
| EP | 1839596 A2 | 2/2008 |
| EP | 1897502 A1 | 3/2008 |
| EP | 1702568 B1 | 7/2008 |
| EP | 1759645 B1 | 11/2008 |
| EP | 1749486 B1 | 3/2009 |
| FR | 999646 A | 2/1952 |
| FR | 1112936 A | 3/1956 |
| FR | 2765794 A | 1/1999 |
| GB | 939929 A | 10/1903 |
| GB | 1210522 A | 10/1970 |
| GB | 2336214 A | 10/1999 |
| JP | 6007357 A | 1/1994 |
| JP | 7051273 A | 2/1995 |
| JP | 8033641 A | 2/1996 |
| JP | 8229050 A | 9/1996 |
| JP | 2000287987 A | 10/2000 |
| JP | 2001286477 A | 10/2001 |
| JP | 2002369820 A | 12/2002 |
| JP | 2005505322 T | 2/2005 |
| JP | 2005103293 A | 4/2005 |
| RU | 2187249 C2 | 8/2002 |
| RU | 2225170 C2 | 3/2004 |
| SU | 1377053 A1 | 2/1988 |
| SU | 1561964 A1 | 5/1990 |
| SU | 1722476 A1 | 3/1992 |
| WO | WO 93/08755 A1 | 5/1993 |
| WO | WO 95/18572 A1 | 7/1995 |
| WO | WO 95/23557 A1 | 9/1995 |
| WO | WO 95/29639 A1 | 11/1995 |
| WO | WO 96/22055 A1 | 7/1996 |
| WO | WO 96/36464 A1 | 11/1996 |
| WO | WO 97/34533 A1 | 9/1997 |
| WO | WO 97/39688 A2 | 10/1997 |
| WO | WO 98/17180 A1 | 4/1998 |
| WO | WO 98/30153 A1 | 7/1998 |
| WO | WO 99/12483 A1 | 3/1999 |
| WO | WO 99/15086 A1 | 4/1999 |
| WO | WO 99/34744 A1 | 7/1999 |
| WO | WO 99/45849 A1 | 9/1999 |
| WO | WO 00/24322 A1 | 5/2000 |
| WO | WO 00/57796 A1 | 10/2000 |
| WO | WO 00/64365 A1 | 11/2000 |
| WO | WO 00/72762 A1 | 12/2000 |
| WO | WO 00/72765 A1 | 12/2000 |
| WO | WO 01/05702 A1 | 1/2001 |
| WO | WO 01/10482 A1 | 2/2001 |
| WO | WO 01/54594 A1 | 8/2001 |
| WO | WO 01/62153 A2 | 8/2001 |
| WO | WO 01/62162 A1 | 8/2001 |
| WO | WO 01/62164 A2 | 8/2001 |
| WO | WO 01/91646 A1 | 12/2001 |
| WO | WO 02/07608 A2 | 1/2002 |
| WO | WO 02/07618 A1 | 1/2002 |
| WO | WO 02/17799 A1 | 3/2002 |
| WO | WO 02/19920 A1 | 3/2002 |
| WO | WO 02/30297 A2 | 4/2002 |
| WO | WO 02/32322 A2 | 4/2002 |
| WO | WO 02/43571 A2 | 6/2002 |
| WO | WO 02/058568 A1 | 8/2002 |
| WO | WO 02/060328 A1 | 8/2002 |
| WO | WO 02/067785 A2 | 9/2002 |
| WO | WO 02/098302 A1 | 12/2002 |
| WO | WO 03/000138 A2 | 1/2003 |
| WO | WO 03/001329 A2 | 1/2003 |
| WO | WO 03/013363 A1 | 2/2003 |
| WO | WO 03/020106 A2 | 3/2003 |
| WO | WO 03/020139 A2 | 3/2003 |
| WO | WO 03/079909 A3 | 3/2003 |
| WO | WO 03/030743 A2 | 4/2003 |
| WO | WO 03/037193 A1 | 5/2003 |
| WO | WO 03/047436 A3 | 6/2003 |
| WO | WO 03/057048 A1 | 7/2003 |
| WO | WO 03/057058 A1 | 7/2003 |
| WO | WO 03/063694 A1 | 8/2003 |
| WO | WO 03/077769 A1 | 9/2003 |
| WO | WO 03/082126 A1 | 10/2003 |
| WO | WO 03/088845 A2 | 10/2003 |
| WO | WO 03/090630 A2 | 11/2003 |
| WO | WO 03/094743 A1 | 11/2003 |
| WO | WO 03/094745 A1 | 11/2003 |
| WO | WO 03/094746 A1 | 11/2003 |
| WO | WO 03/094747 A1 | 11/2003 |
| WO | WO 03/101313 A1 | 12/2003 |
| WO | WO 03/105698 A2 | 12/2003 |
| WO | WO 03/105702 A2 | 12/2003 |
| WO | WO 2004/006980 A2 | 1/2004 |
| WO | WO 2004/028585 A2 | 4/2004 |
| WO | WO 2004/032754 A2 | 4/2004 |
| WO | WO 2004/032760 A2 | 4/2004 |
| WO | WO 2004/032762 A1 | 4/2004 |
| WO | WO 2004/032763 A2 | 4/2004 |
| WO | WO 2004/047653 A2 | 6/2004 |
| WO | WO 2004/049956 A2 | 6/2004 |
| WO | WO 2004/086987 A1 | 10/2004 |
| WO | WO 2004/096057 A2 | 11/2004 |
| WO | WO 2004/105621 A1 | 12/2004 |
| WO | WO 2004/112618 A2 | 12/2004 |
| WO | WO 2004/112652 A2 | 12/2004 |
| WO | WO 2005/027983 A2 | 3/2005 |
| WO | WO 2005/037329 A2 | 4/2005 |
| WO | WO 2005/078892 A1 | 8/2005 |
| WO | WO 2005/096954 A2 | 10/2005 |
| WO | WO 2005/112808 A1 | 12/2005 |
| WO | WO 2005/115251 A2 | 12/2005 |
| WO | WO 2006/044490 A2 | 4/2006 |
| WO | WO 2006/044581 A2 | 4/2006 |
| WO | WO 2006/044810 A2 | 4/2006 |
| WO | WO 2006/083748 A1 | 8/2006 |
| WO | WO 2006/115958 A1 | 11/2006 |
| WO | WO 2006/132992 A1 | 12/2006 |
| WO | WO 2007/016290 A2 | 2/2007 |
| WO | WO 2007/018898 A2 | 2/2007 |
| WO | WO 2007/121579 A1 | 11/2007 |
| WO | WO 2007/139734 A2 | 12/2007 |
| WO | WO 2007/142625 A2 | 12/2007 |
| WO | WO 2008/039270 A1 | 4/2008 |
| WO | WO 2008/045383 A2 | 4/2008 |

OTHER PUBLICATIONS

Disclosed Anonymously, "Motor-Driven Surgical Stapler Improvements," Research Disclosure Database No. 526041, Published: Feb. 2008.

C.C. Thompson at al., "Peroral Endoscopic Reduction of Dilated Gastrojejunal Anastomosis After Roux-en-Y Gastric Bypass: A Possible New Option for Patients with Weight Regain," Surg Enclose (2006) vol. 20, pp. 1744-1748.

B.R. Coolman, DVM, MS et al., "Comparison of Skin Staples With Sutures for Anastomosis of the Small Intestine in Dogs," Abstract; http://www.blackwell-synergy.com/doi/abs/10.1053/jvet.2000.

7539?cookieSet=1&journalCode=vsu which redirects to http://www3.interscience.wiley.com/journal/119040681/abstract?CRETRY=1&SRETRY=0; [online] accessed: Sep. 22, 2008 (2 pages).
U.S. Appl. No. 12/031,001, filed Feb. 14, 2008.
U.S. Appl. No. 12/031,611, filed Feb. 14, 2008.
U.S. Appl. No. 11/729,008, filed Mar. 28, 2007.
U.S. Appl. No. 11/821,277, filed Jun. 22, 2007.

U.S. Appl. No. 12/031,368, filed Feb. 14, 2008.
U.S. Appl. No. 12/031,326, filed Feb. 14, 2008.
U.S. Appl. No. 12/030,980, filed Feb. 14, 2008.
U.S. Appl. No. 12/031,066, filed Feb. 14, 2008.
U.S. Appl. No. 12/031,030, filed Feb. 14, 2008.
U.S. Appl. No. 12/030,974, filed Feb. 14, 2008.

* cited by examiner

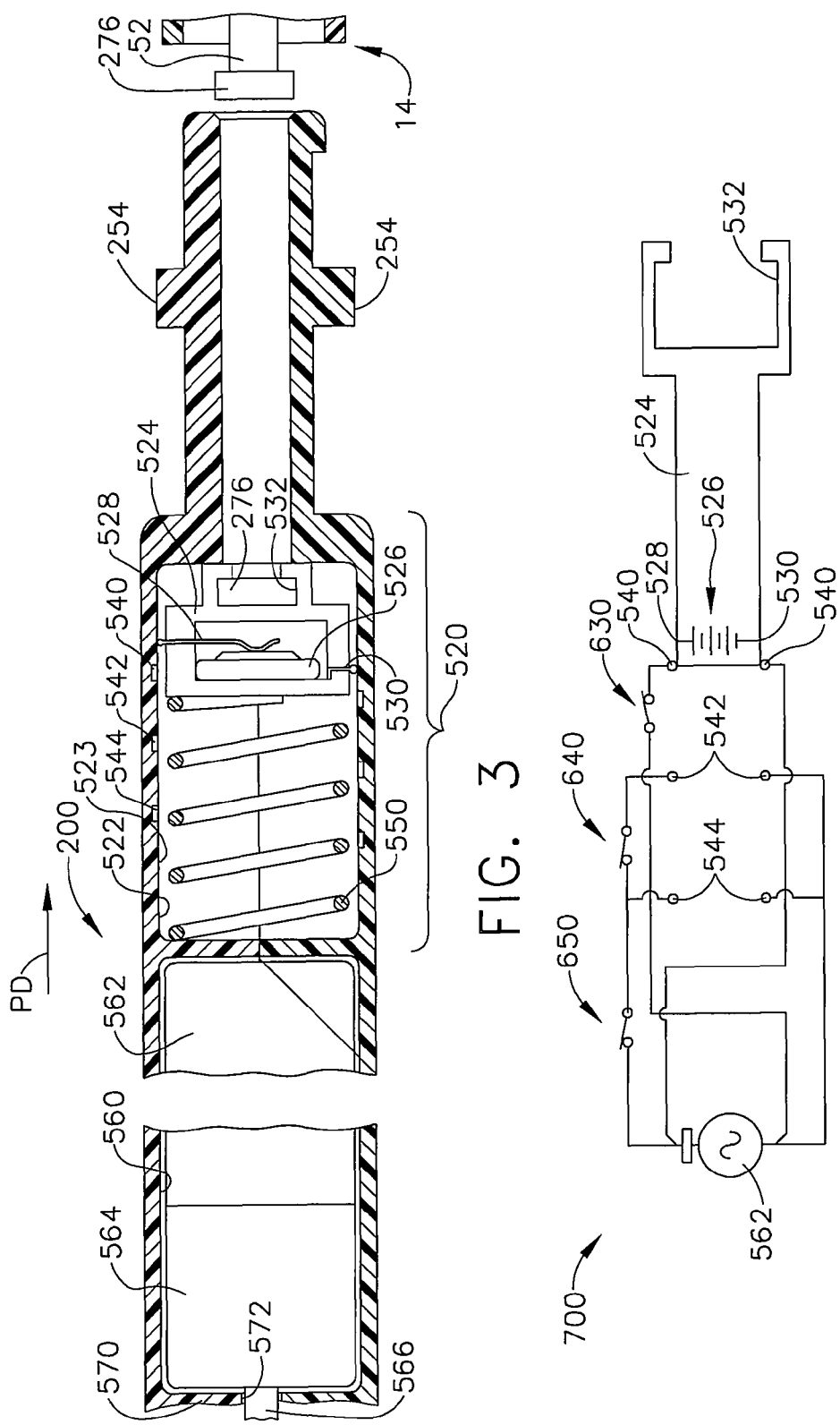

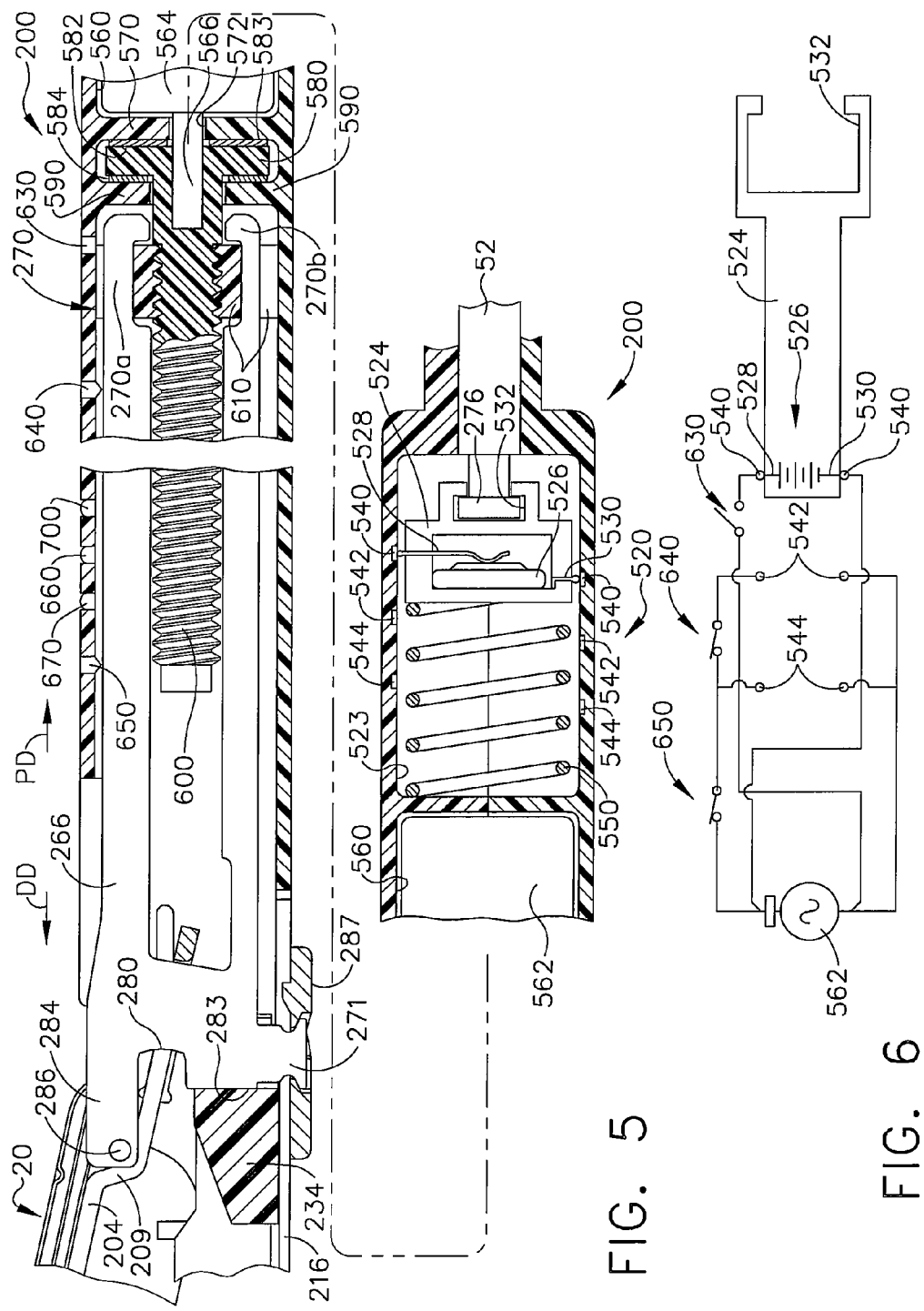

DISPOSABLE MOTOR-DRIVEN LOADING UNIT FOR USE WITH A SURGICAL CUTTING AND STAPLING APPARATUS

FIELD OF THE INVENTION

The present invention relates in general to endoscopic surgical instruments including, but not limited to, surgical cutting and stapling apparatuses that have disposable loading units that are capable of applying lines of staples to tissue while cutting the tissue between those staple lines and, more particularly, to improvements relating to such disposable loading units.

BACKGROUND

Endoscopic surgical instruments are often preferred over traditional open surgical devices since a smaller incision tends to reduce the post-operative recovery time and complications. Consequently, significant development has gone into a range of endoscopic surgical instruments that are suitable for precise placement of a distal end effector at a desired surgical site through a cannula of a trocar. These distal end effectors engage the tissue in a number of ways to achieve a diagnostic or therapeutic effect (e.g., endocutter, grasper, cutter, staplers, clip applier, access device, drug/gene therapy delivery device, and energy device using ultrasound, RF, laser, etc.).

Known surgical staplers include an end effector that simultaneously makes a longitudinal incision in tissue and applies lines of staples on opposing sides of the incision. The end effector includes a pair of cooperating jaw members that, if the instrument is intended for endoscopic or laparoscopic applications, are capable of passing through a cannula passageway. One of the jaw members supports a staple cartridge that has at least two laterally spaced rows of staples. The other jaw member defines an anvil having staple-forming pockets aligned with the rows of staples in the cartridge. The instrument commonly includes a plurality of reciprocating wedges which, when driven distally, pass through openings in the staple cartridge and engage drivers supporting the staples to effect the firing of the staples toward the anvil.

One type of surgical stapling apparatus is configured to operate with disposable loading units (DLU's) that are constructed to support a staple cartridge and knife assembly therein. Once the procedure is completed, the entire DLU is discarded. Such instruments that are designed to accommodate DLU's purport to offer the advantage of a "fresh" knife blade for each firing of the instrument. Examples of such surgical stapling apparatuses and DLU's are disclosed in U.S. Pat. No. 5,865,361 to Milliman et al., the disclosure of which is herein incorporated by reference in its entirety.

Such prior disposable loading units, however, require the clinician to continuously ratchet the handle to fire the staples and cut the tissue. There is a need for a surgical stapling apparatus configured for use with a disposable loading unit that is driven by a motor contained in the disposable loading unit.

SUMMARY

In one general aspect of various embodiments of the present invention, there is provided a disposable loading unit for attachment to a surgical cutting and stapling apparatus. In various embodiments, the disposable loading unit may comprise a carrier that supports a staple cartridge therein. An anvil assembly may be movably coupled to the carrier for selective movable travel between open and closed positions relative to the staple cartridge. An axial drive assembly may be supported within the carrier such that it can move in a distal direction from a start position to an end position through the carrier and the staple cartridge. The axial drive assembly may also be retracted in a proximal direction from the end position back to the start position. A motor may be supported within the carrier and constructed to drive the axial drive assembly in the distal and proximal directions. A battery may be supported within the carrier and be coupled to the motor for supplying power thereto.

In still another general aspect of various embodiments of the present invention, there is provided a disposable loading unit for attachment to a surgical cutting and stapling apparatus. In various embodiments, the disposable loading unit includes a carrier that supports a staple cartridge therein. An anvil assembly may be movably coupled to the carrier for selective movable travel between open and closed positions relative to the staple cartridge. A housing may be coupled to the carrier and be configured for removable operable attachment to the surgical stapling apparatus. An axial drive assembly may be supported within the carrier and the housing to move in a distal direction from a start position to an end position through the carrier and the staple cartridge. The axial drive assembly may also be retracted in a proximal direction from the end position to the start position. A motor may be supported within the carrier and configured to interface with the axial drive assembly to drive the axial drive assembly in the distal and proximal directions. A battery may be supported within the carrier and be coupled to the motor for supplying power thereto. The battery may be selectively movable between a disconnected position and connected positions in response to motions applied thereto by a portion of the surgical stapling apparatus.

In another general aspect of various embodiments of the present invention, there is provided a surgical cutting and stapling apparatus. Various embodiments of the instrument may include a handle assembly that operably supports a drive assembly therein that is constructed to impart drive motions and a retraction motion. A movable handle portion may be operably supported on the handle assembly and configured to interface with the drive system such that manipulation of the movable handle causes the drive system to impart the drive motions. An elongated body may protrude from the handle assembly and have a distal end that is couplable to a disposable loading unit. In various embodiments, the disposable loading unit may comprise a carrier that has a staple cartridge supported therein. An anvil assembly may be movably coupled to the carrier for selective movable travel between open and closed positions relative to the staple cartridge. An axial drive assembly may be supported within the carrier such that the axial drive assembly may move in a distal direction from a start position to an end position through the carrier and the staple cartridge and also in a proximal direction from the end position to the start position. A motor may be supported within the carrier and configured to interface with the axial drive assembly to drive the axial drive assembly in the distal and proximal directions. A battery may be supported within the carrier and be coupled to the motor for supplying power thereto. The battery may be configured to interface with a portion of the elongated body to receive the drive motions therefrom upon manipulation of the moveable handle.

These and other objects and advantages of the present invention shall be made apparent from the accompanying drawings and the description thereof.

BRIEF DESCRIPTION OF THE FIGURES

The accompanying drawings, which are incorporated in and constitute a part of this specification, illustrate embodiments of the invention, and, together with the general description of various embodiments of the invention given above, and the detailed description of the embodiments given below, serve to explain various principles of the present invention.

FIG. 3 is a cross-sectional view of a proximal end of the disposable loading unit embodiment of FIGS. 1 and 2 with various components shown in full view for clarity.

FIG. 4 is a schematic of a circuit embodiment of the disposable loading unit of FIGS. 1-3.

FIG. 5 is a cross-sectional view of the disposable loading unit of FIGS. 1-3 when the disposable loading unit has been attached to the elongated body of the surgical instrument.

FIG. 6 is a schematic view of the circuit illustrating the position of various components of the disposable loading unit after it has been attached to the surgical instrument.

DETAILED DESCRIPTION

Figure 1:
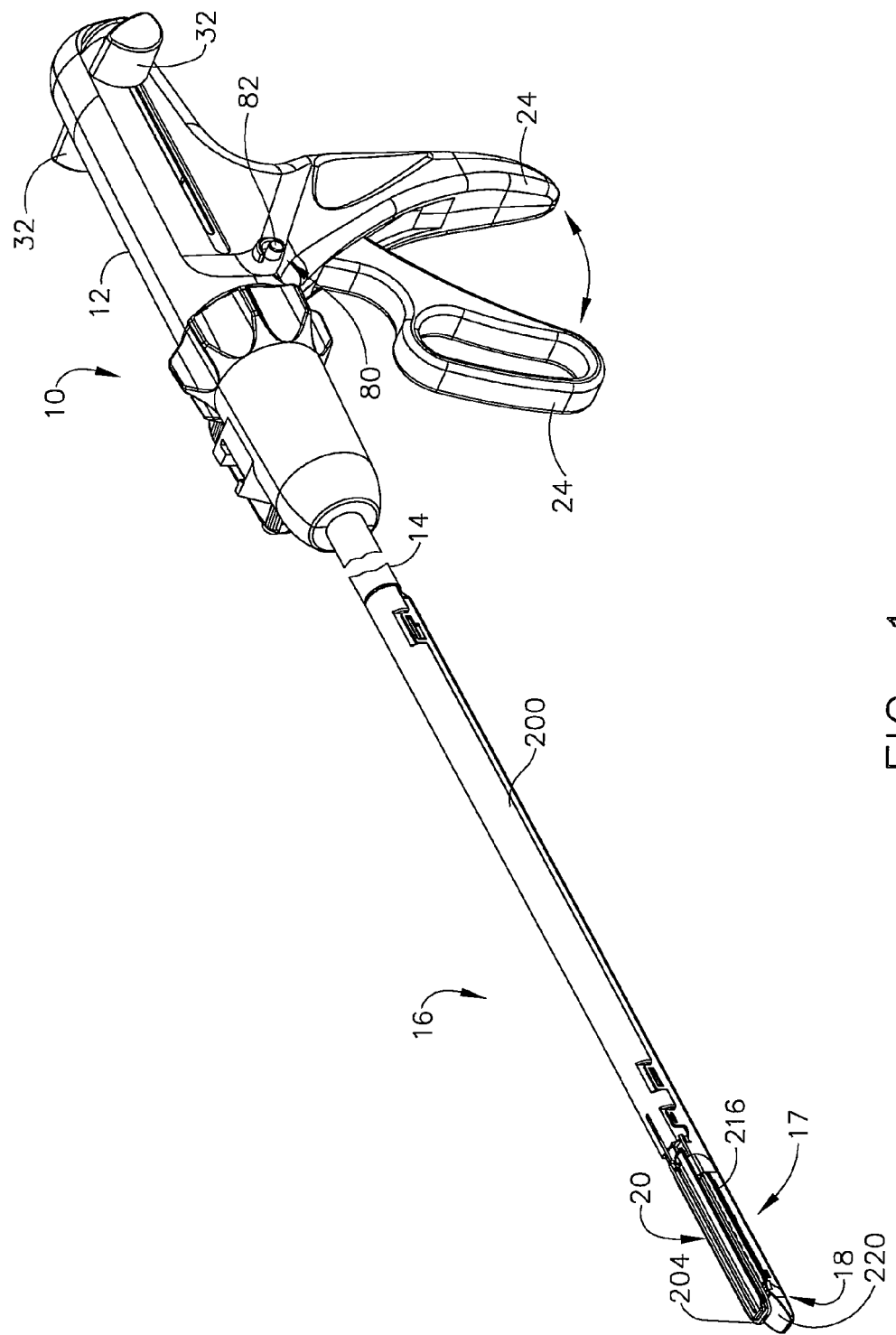
FIG. 1 is a perspective view of a disposable loading unit embodiment of the present invention coupled to a conventional surgical cutting and stapling apparatus.

Turning to the Drawings, wherein like numerals denote like components throughout the several views, FIG. 1 depicts a disposable loading unit 16 of the present invention that is coupled to a conventional surgical cutting and stapling apparatus 10. The construction and general operation of a cutting and stapling apparatus 10 is described in U.S. Pat. No. 5,865,361, the disclosure of which has been herein incorporated by reference. Thus, the present Detailed Description will not discuss the various components of the apparatus 10 and their operation herein beyond what is necessary to describe the operation of the disposable loading unit 16 of the present invention.

As the present Detailed Description proceeds, it will be appreciated that the terms "proximal" and "distal" are used herein with reference to a clinician gripping a handle assembly 12 of the surgical stapling apparatus 10 to which the disposable loading unit 16 is attached. Thus, the disposable loading unit 16 is distal with respect to the more proximal handle assembly 12. It will be further appreciated that, for convenience and clarity, spatial terms such as "vertical", "horizontal", "up", "down", "right", and "left" are used herein with respect to the drawings. However, surgical instruments are used in many orientations and positions, and these terms are not intended to be limiting and absolute.

Figure 2:
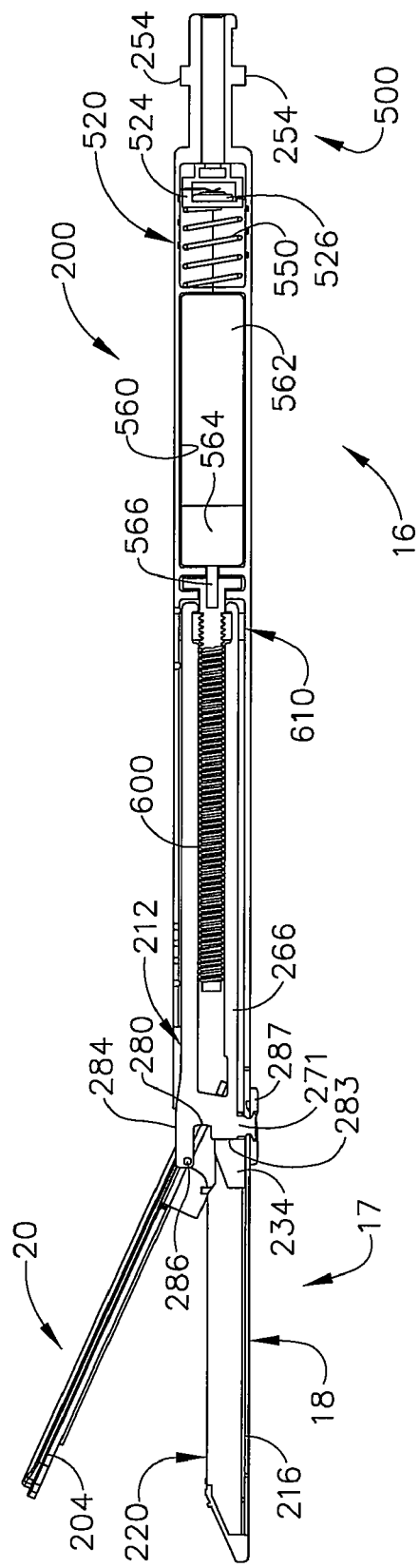
FIG. 2 is a cross-sectional view of the disposable loading unit of FIG. 1 with several components shown in full view for clarity.

As can be seen in FIG. 1, the disposable loading unit 16 may generally comprise a tool assembly 17 for performing surgical procedures such as cutting tissue and applying staples on each side of the cut. The tool assembly 17 may include a cartridge assembly 18 that includes a staple cartridge 220 that is supported in a carrier 216. An anvil assembly 20 may be pivotally coupled to the carrier 216 in a known manner for selective pivotal travel between open and closed positions. The anvil assembly 20 includes an anvil portion 204 that has a plurality of staple deforming concavities (not shown) formed in the undersurface thereof. The staple cartridge 220 houses a plurality of pushers or drivers (not shown) that each have a staple or staples (not shown) supported thereon. An actuation sled 234 is supported within the tool assembly 17 and is configured to drive the pushers and staples in the staple cartridge 220 in a direction toward the anvil assembly 20 as the actuation sled 234 is driven from the proximal end of the tool assembly 17 to the distal end 220. See FIG. 2.

The disposable loading unit 16 may further include an axial drive assembly 212 that comprises a drive beam 266 that may be constructed from a single sheet of material or, preferably, from multiple stacked sheets. However, the drive beam 266 may be constructed from other suitable material configurations. The distal end of drive beam 266 may include a vertical support strut 271 which supports a knife blade 280 and an abutment surface 283 which engages the central portion of actuation sled 234 during a stapling procedure. Knife blade 280 may be generally positioned to translate slightly behind actuation sled 234 through a central longitudinal slot in staple cartridge 220 to form an incision between rows of stapled body tissue. A retention flange 284 may project distally from vertical strut 271 and support a camming pin or pins 286 at its distal end. Camming pin 286 may be dimensioned and configured to engage camming surface 209 on anvil portion 204 to clamp anvil portion 204 against body tissue. See FIGS. 5 and 7. In addition, a leaf spring (not shown) may be provided between the proximal end of the anvil portion 204 and the distal end portion of the housing 200 to bias the anvil assembly 20 to a normally open position. The carrier 216 may also have an elongated bottom slot therethrough through which a portion of the vertical support strut 271 extends to have a support member 287 attached thereto As can also be seen in FIG. 1, the disposable loading unit 16 may also have a housing portion 200 that is adapted to snap onto or otherwise be attached to the carrier 216. The proximal end 500 of housing 200 may include engagement nubs 254 for releasably engaging elongated body 14 of a surgical stapling apparatus. Nubs 254 form a bayonet type coupling with the distal end of the elongated body portion 14 of the surgical stapling apparatus as described in U.S. Pat. No. 5,865,361.

The housing 200 may further include a switch portion 520 that movably houses a battery 526 therein. More specifically and with reference to FIG. 3, the switch portion 520 of the housing 200 defines a battery cavity 522 that movably supports a battery holder 524 that houses a battery 526 therein. As can be seen in FIG. 3, a first battery contact 528 is supported in electrical contact with the battery 526 and protrudes out through the battery holder 524 for sliding engagement with the inside wall 523 of the battery cavity 522. Similarly, a second battery contact 530 is mounted in electrical contact with the battery 526 and also protrudes out of the battery holder 524 to slide along the inside wall 523 of the battery cavity 522. The battery holder 524 has a control rod socket 532 therein configured to receive the distal end 276 of control rod 52 when the proximal end of disposable loading unit 16 is coupled to the elongated body 14 of surgical stapling apparatus 10. As can also be seen in FIG. 3, a series of contacts 540, 542, 544 may be oriented within the wall 523 for contact with the battery contacts 530. The purpose of the contacts 540, 542, and 544 will be discussed in further detail below. As can also be seen in FIG. 3, a biasing member or switch spring 550 is positioned within the battery cavity 522 to bias the battery holder 524 in the proximal direction "PD" such that when the disposable reload 16 is not attached to the elongated body 14, the battery holder 524 is biased to its proximal-most position shown in FIG. 3. When retained in that "pre-use" or "disconnected" position by spring 550, the battery contacts 528 and 530 do not contact any of the contacts 540, 542, 544 within the battery cavity 522 to prevent the battery 526 from being drained during non-use.

As can also be seen in FIG. 3, the housing 200 may further have a motor cavity 560 therein that houses a motor 562 and a gear box 564. The gear box 564 has an output shaft 566 that protrudes through a hole 572 in a proximal bulkhead 570 formed in the housing 200. See FIG. 5. The output shaft 566 is keyed onto or otherwise non-rotatably coupled to a thrust disc 580. As can be seen in FIG. 5, the thrust disc 580 is rotatably supported within a thrust disc cavity 582 formed between the proximal bulkhead 570 and a distal bulkhead 590 formed in the housing 200. In addition, the thrust disc 580 is rotatably supported between a proximal thrust bearing 583 and a distal thrust bearing 584 as shown. As can also be seen in FIG. 5, the thrust disc 580 may be formed on a proximal end of a drive screw 600 that threadedly engages a drive nut 610 that is supported within an engagement section 270 formed on the distal end of the drive beam 266. In various embodiments, the engagement section 270 may include a pair of engagement fingers 270a and 270b that are dimensioned and configured to be received within a slot in the drive nut 610 to non-rotatably affix the drive nut 610 to the drive beam 266. Thus, rotation of the drive screw 600 within the drive nut 610 will drive the drive beam 266 in the distal direction "DD" or in the proximal direction "PD" depending upon the direction of rotation of the drive screw 600.

The disposable loading unit 16 may further include a return switch 630 that is mounted in the housing 200 and is adapted to be actuated by the knife nut 610. As can also be seen in FIG. 5, a switch 640 is mounted in the housing 200 and is also oriented to be actuated by the knife nut 610 to indicate when the anvil assembly 20 has been closed. A switch 650 is mounted in the housing 200 and is also adapted to be actuated by the knife nut 610 to indicate that the axial drive assembly 212 has moved to is finished position. The specific operations of switches 630, 640, 650 will be discussed in further detail below.

FIG. 4 illustrates a circuit embodiment 700 of the present invention that illustrates the positions of various components of the disposable loading unit 16 of the present invention when in a "pre-use" condition. For example, the various components of the disposable loading unit 16 may be in this pre-use orientation when the unit 16 is being stored or shipped. As can be seen in that Figure, when in this orientation, the battery contacts 528 and 530 do not contact any of the contacts 540, 542, 544 in the housing 200 which prevents the battery 526 from being drained during non-use.

FIGS. 5 and 6 illustrate the positions of various components of the disposable loading unit 16 after it has been coupled to the elongated body 14 of the surgical cutting and stapling instrument 10. In particular, as can be seen in FIG. 5, the distal end 276 of the control rod 52 has been coupled to the battery holder 524. When the control rod 52 is attached to the battery holder 524, the battery holder 524 is moved in the distal direction "DD" against the spring 550 such that the battery contacts 528, 530 are brought into contact with the return contacts 540 in the housing 200. Also, when in that position, the knife nut 610 actuates the return switch 630 into an open orientation. It will be appreciated that the return switch 630 is a normally closed switch that is actuated to the open position by the knife nut 610. As shown in FIG. 6, when the return switch 630 is open, the motor 562 is not powered.

Figure 7:
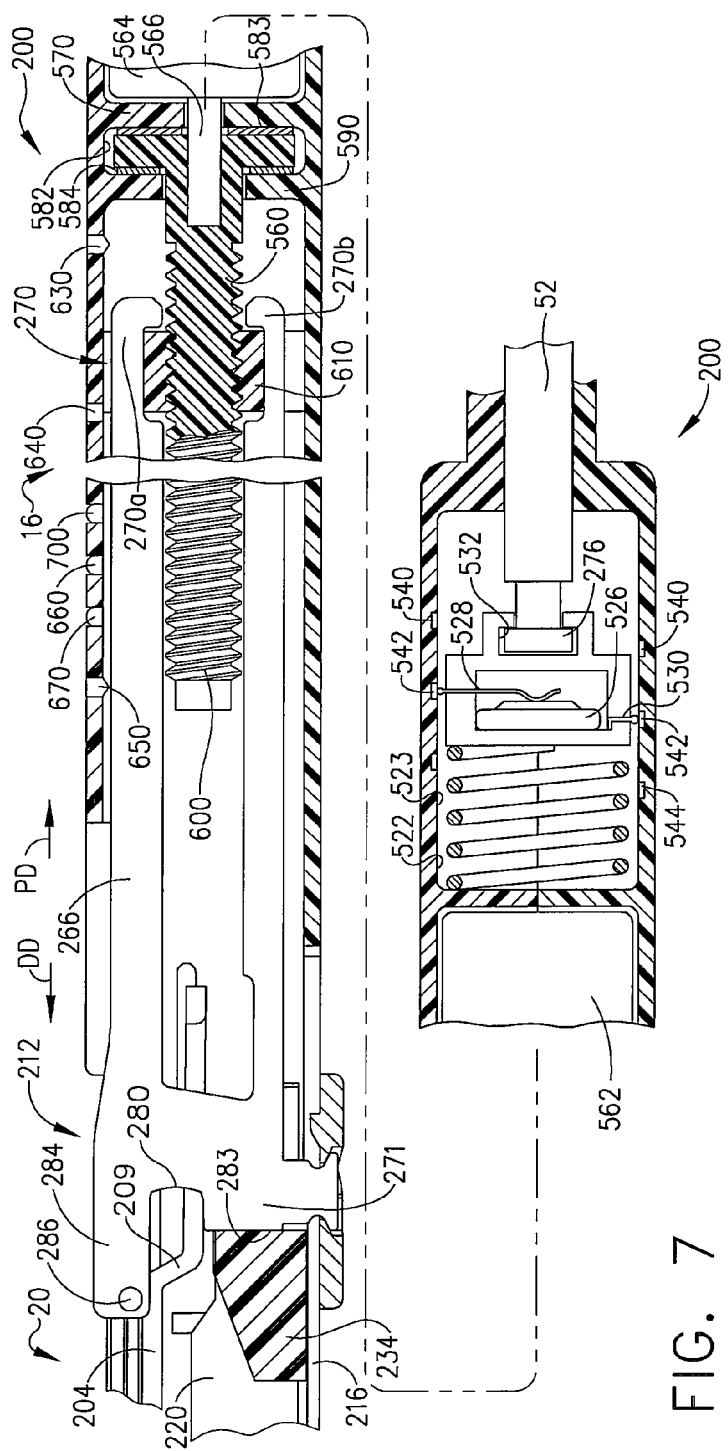
FIG. 7 is a cross-sectional view of the disposable loading unit of FIGS. 1-6 when the drive beam has been moved to the anvil closed position.
Figure 8:
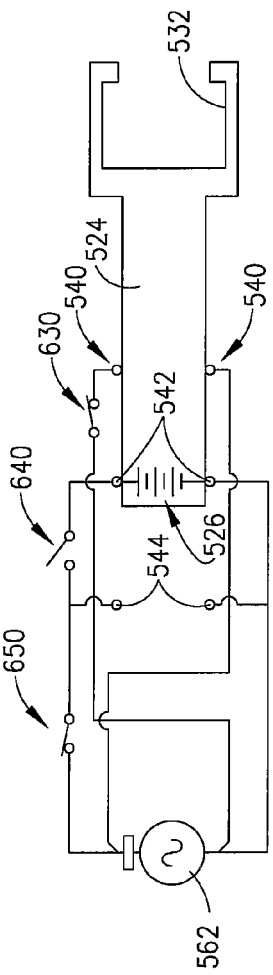
FIG. 8 is a schematic view of the circuit illustrating the position of various components of the disposable loading unit after the drive beam has been moved to the anvil closed position.

FIGS. 7 and 8 illustrate the positions of various components of the disposable loading unit 16 after the clinician has actuated the movable handle 24 (shown in FIG. 1) of the surgical cutting and stapling instrument 10. As discussed in U.S. Pat. No. 5,865,361, when the movable handle 24 is initially moved toward the stationary handle member 22, the control rod 52 is caused to move in the distal direction "DD". As can be seen in FIG. 7, as the control rod 52 is initially moved in the distal direction during the anvil close stroke, the battery holder 524 moves the battery 526 to a position wherein the battery contacts 528, 530 contact the anvil close contacts 542. Power is now permitted to flow from the battery 526 to the motor 562 which rotates the drive screw 600 and causes the drive beam 266 to move distally. As the drive beam 266 moves distally in the "DD" direction, the camming pin 286 engages cam portion 209 of anvil portion 204 and causes the anvil assembly 20 to pivot to a closed position as illustrated in FIG. 7. As the drive beam 266 moves distally to the anvil closed position, the knife nut 610 moves out of contact with the return switch 630 which permits the return switch to resume its normally open position. The knife nut 610 then actuates the anvil closed switch 640 and moves it to an open position. See FIG. 8. In various embodiments one or more anvil closed lights 660 may be mounted in the housing 200 for providing a visual indication to the clinician that the anvil assembly 20 has been moved to the closed position.

Figure 9:
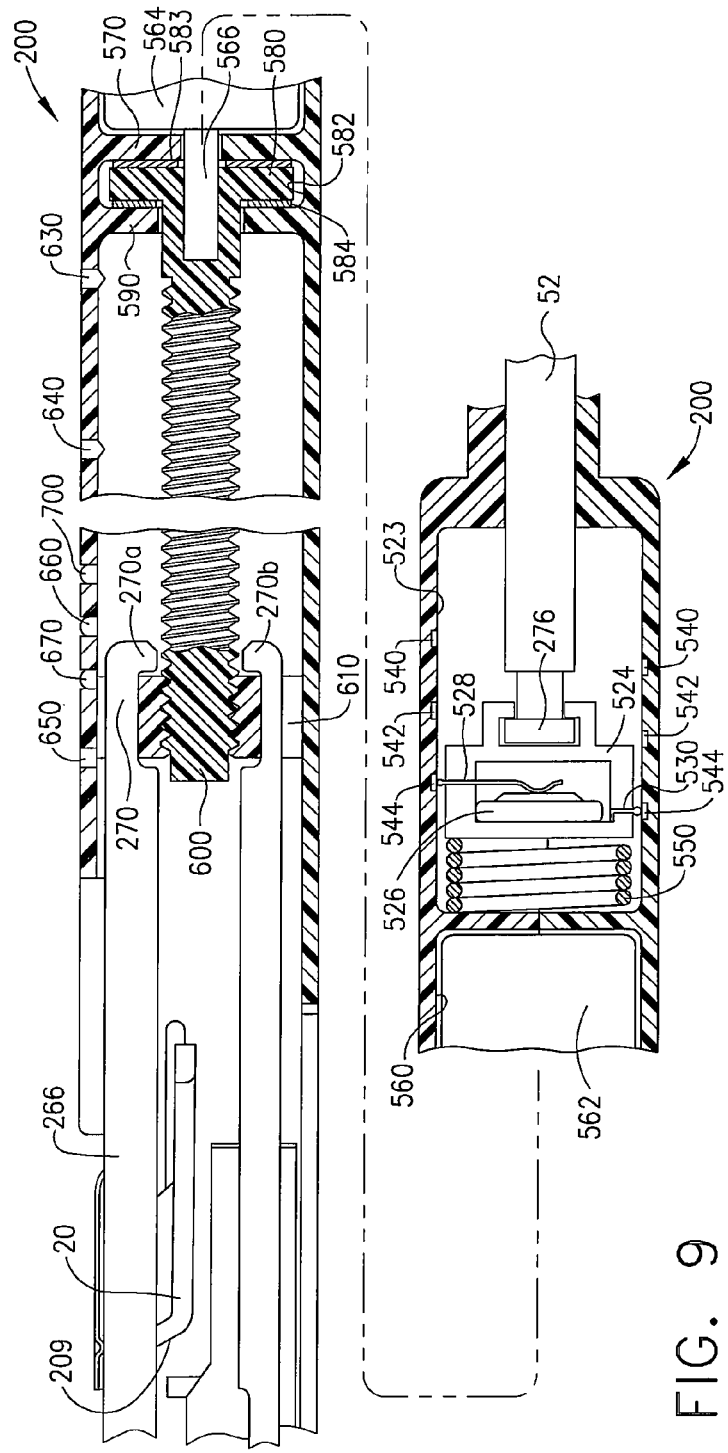
FIG. 9 is a cross-sectional view of the disposable loading unit of FIGS. 1-8 when the drive beam has been moved to its distal-most fired position.
Figure 10:
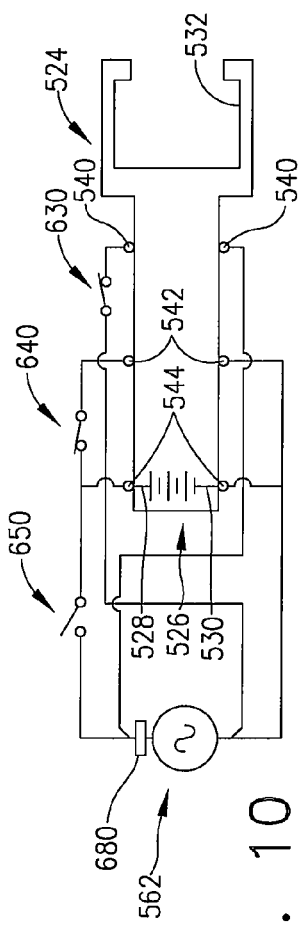
FIG. 10 is a schematic view of the circuit illustrating the position of various components of the disposable loading unit after the drive beam has been moved to its distal-most fired position.

When the clinician desires to fire the instrument 10 (i.e., actuate the instrument 10 to cause it to cut and staple tissue), the clinician first depresses the plunger 82 of the firing lockout assembly 80 (FIG. 1) as discussed in U.S. Pat. No. 5,865,361. Thereafter, movable handle 24 may be actuated. As the movable handle 24 is depressed, the control rod 52 moves the battery holder 524 and battery 526 to the position illustrated in FIGS. 9 and 10. As can be seen in those Figures, when the battery 526 is moved into that position, the battery contacts 528, 530 are brought into contact with the fire contacts 544. The switch 650 is normally closed until it is actuated by the knife nut 610. Thus, when the battery contacts 528, 530 contact the firing contacts 544, power flows from the battery 526 to the motor 562 which drives the drive screw 600. As the drive screw 600 is rotated, the drive beam 266 and knife nut 610 are driven in the distal direction "DD" to advance actuation sled 234 through staple cartridge 220 to effect ejection of staples and cutting of tissue. Once the drive beam 266 reaches the end of the firing stroke (i.e., all of the staples in the staple cartridge 220 have been fired), knife nut 610 is positioned to actuate the normally closed switch 650 and move it to an open position (illustrated in FIG. 10) which stops the flow of power from the battery 526 to the motor 562. In various embodiments, a distal indication light or lights 670 may be mounted on the housing 200 to provide an indication to the clinician that the drive beam 266 has reached its distal-most fired position.

To retract the drive beam 266, the clinician grasps the retract knobs 32 (shown in FIG. 1) on the handle assembly 12 and pulls them in the proximal direction "PD". The operation and construction of the retract knobs 32 is discussed in U.S. Pat. No. 5,865,361. Once the clinician moves the drive beam 266 a sufficient distance in the proximal direction "PD" so as to move the battery to contacts 540 (FIG. 11), power will be supplied through switch 630 to reverse the motor 562. Knife nut then releases switch 650. The motor 562 then drives the drive beam 266 distal to switch 630, which opens. The return switch 630 is also in its normally closed position thereby permitting power to flow to the motor 562 and rotate the drive screw 610 in an opposite direction to drive the drive beam 266 in the proximal direction "PD". Once the knife nut 610 actuates the knife return switch 630, the knife return switch 630 is moved to an open position thereby stopping flow of power from the battery 526 to the motor 562. In various embodiments, a starting light 700 may be mounted in the housing 200 to provide an indication that the drive beam 266 is in the starting position.

Figure 11:
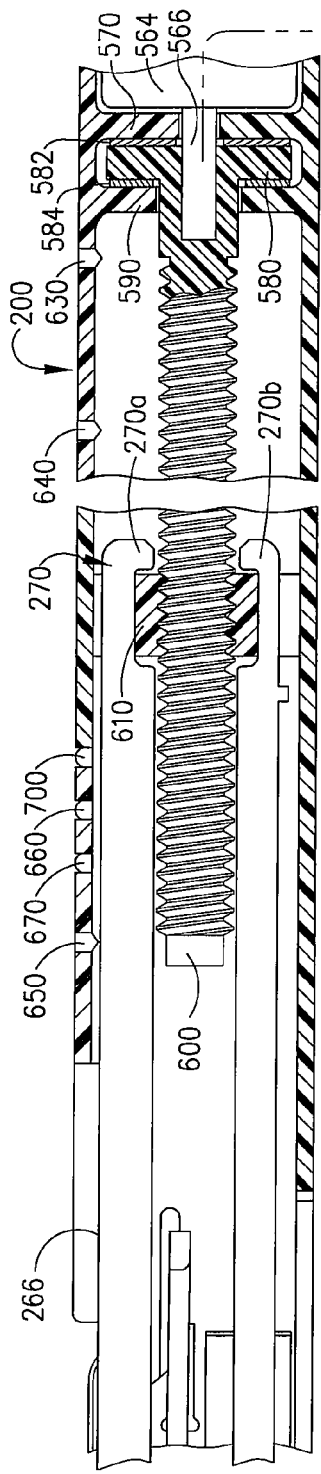
FIG. 11 is a cross-sectional view of the disposable loading unit of FIGS. 1-10 as the drive beam is being returned to a starting position.
Figure 12:
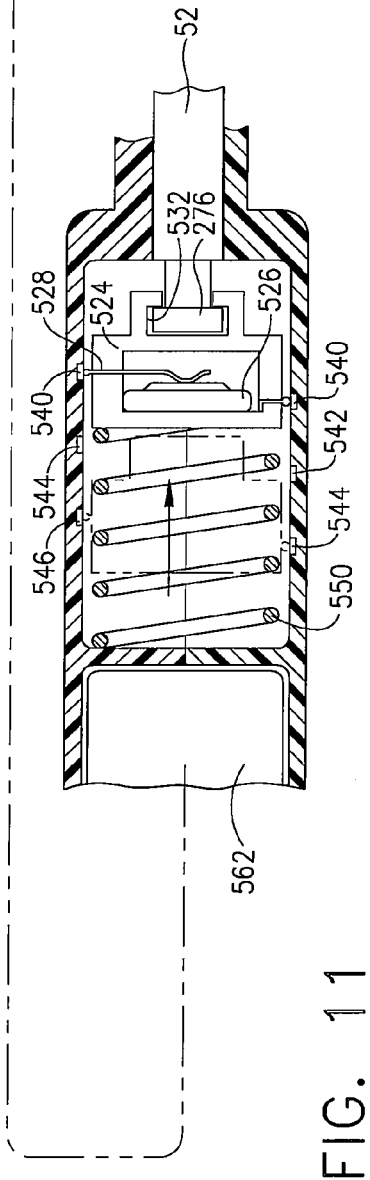
FIG. 12 is a schematic view of the circuit illustrating the position of various components of the disposable loading unit as the drive beam is being returned to a start position.

FIGS. 11 and 12 illustrate the positions of various components of the disposable loading unit 16 of the present invention when the distal end of the drive beam 266 and blade 280 inadvertently becomes jammed during the firing stroke (i.e., when the blade 280 is being distally advanced through the tissue clamped in the tool assembly 17). To address such occurrence, a current limiter 680 may be provided as shown in FIG. 12. The current limiter 680 serves to turn off the motor 562 when the amount of current that it is drawing exceeds a predetermined threshold. It will be understood that the amount of current that the motor 562 draws during a jam would increase over the amount of current drawn during normal firing operations. Once the current limiter 680 shuts down the motor 562, the clinician can retract the drive beam 266 by grasping the retract knobs 32 (shown in FIG. 1) on the handle assembly 12 and pulling them in the proximal direction "PD" and the motor 562 will drive the drive screw 600 in reverse in the manner described above. Thus, the current limiter 680 serves to stop the motor 562 when the axial drive assembly 212 encounters resistance that exceeds a predetermined amount of resistance which is associated with the predetermined maximum amount of current that the motor 562 should draw under normal operating circumstances. This feature also saves the battery power so the drive beam 266 can be retracted.

Thus, the disposable loading unit 16 of the present invention comprises a self-contained motor driven disposable loading unit that may be used in connection with conventional surgical cutting and stapling instruments that traditionally required the clinician to manually advance and retract the drive assembly and cutting blade of a disposable loading unit coupled thereto. Various embodiments of the disposable loading unit 16 may be constructed to facilitate the automatic retraction of the axial drive assembly should the blade encounter a predetermined amount of resistance.

While several embodiments of the invention have been described, it should be apparent, however, that various modifications, alterations and adaptations to those embodiments may occur to persons skilled in the art with the attainment of some or all of the advantages of the invention. For example, according to various embodiments, a single component may be replaced by multiple components, and multiple components may be replaced by a single component, to perform a given function or functions. This application is therefore intended to cover all such modifications, alterations and adaptations without departing from the scope and spirit of the disclosed invention as defined by the appended claims.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

The invention which is intended to be protected is not to be construed as limited to the particular embodiments disclosed. The embodiments are therefore to be regarded as illustrative rather than restrictive. Variations and changes may be made by others without departing from the spirit of the present invention. Accordingly, it is expressly intended that all such equivalents, variations and changes which fall within the spirit and scope of the present invention as defined in the claims be embraced thereby.

What is claimed is:

1. A disposable loading unit for attachment to a surgical cutting and stapling apparatus, said disposable loading unit comprising:
   a carrier;
   a staple cartridge supported in said carrier;
   an anvil assembly movably coupled to said carrier for selective movable travel between open and closed positions relative to said staple cartridge;
   an axial drive assembly supported within said carrier to move in a distal direction from a start position to an end position through said carrier and said staple cartridge and in a proximal direction from said end position to said start position;
   a motor supported within said carrier and interfacing with said axial drive assembly to drive said axial drive assembly in said distal and proximal directions;
   a battery holder movably supported within said carrier and attachable to a control rod of the surgical cutting and stapling apparatus; and
   a battery supported within said battery holder such that said battery is retained in a disconnected position prior to coupling said disposable loading unit to the surgical cutting and stapling apparatus and is movable therefrom to at least one subsequent position upon coupling said disposable loading unit to said surgical stapling apparatus.

2. The disposable loading unit of claim 1 further comprising an indicator supported on said disposable loading unit for indicating when said axial drive assembly is in a starting position.

3. The disposable loading unit of claim 1 further comprising an indicator supported on said disposable loading unit for indicating when said anvil assembly is in said closed position.

4. The disposable loading unit of claim 1 further comprising an indicator supported on said disposable loading unit for indicating when said axial drive assembly is in a distal-most position.

5. The disposable loading unit of claim 1 further comprising means for stopping said motor from driving said drive assembly in said proximal direction when said axial drive assembly encounters resistance that exceeds a predetermined amount of resistance.

6. The disposable loading unit of claim 5 wherein said means for stopping said motor comprises a current limiter operably coupled to said motor.

7. A disposable loading unit for attachment to a surgical cutting and stapling apparatus, said disposable loading unit comprising:
   a carrier;
   a staple cartridge supported in said carrier;
   an anvil assembly movably coupled to said carrier for selective movable travel between open and closed positions relative to said staple cartridge;
   a housing coupled to said carrier and configured for removable operable attachment to the surgical cutting and stapling apparatus;
   an axial drive assembly supported within said carrier and said housing to move in a distal direction from a start position to an end position through said carrier and said staple cartridge and in a proximal direction from said end position to said start position;
   a motor supported within said carrier and interfacing with said axial drive assembly to drive said axial drive assembly in said distal and proximal directions;
   a battery holder movably supported within said carrier and attachable to a control member of the surgical cutting and stapling apparatus, said battery holder being movable from a deactivated position to at least one subsequent position upon attachment to the control member; and
   a battery supported within said movable battery holder such that when said battery holder is in said deactivated position, said battery does not supply control power and when said battery holder is moved from said deactivated position to said at least one subsequent position, said battery supplies control power.

8. The disposable loading apparatus of claim 7 wherein said battery is retained in said deactivated position prior to said movable battery housing being coupled to the control member of the surgical cutting and stapling apparatus.

9. The disposable loading unit of claim 8 further comprising means for stopping said motor when said axial drive assembly encounters resistance that exceeds a predetermined amount of resistance.

10. The disposable loading unit of claim 7 further comprising means on said housing for indicating when said axial drive assembly is in a starting position and an ending position.

11. The disposable loading unit of claim 7 further comprising means on said housing for indicating when said anvil is in said closed position.

12. The disposable loading unit of claim 7 further comprising a biasing member within said carrier for biasing said movable battery holder to said deactivated position.

13. The disposable loading unit of claim 7 wherein said at least one subsequent position comprises a first contact arrangement in said carrier such that when said battery is moved into electrical contact with said first contact arrangement, said battery supplies control power therethrough.

14. The disposable loading unit of claim 13 wherein said at least one subsequent position further comprises a second contact arrangement in said carrier such that when said battery is moved into electrical contact with said second contact arrangement, said battery supplies control power therethrough.

15. A surgical cutting and stapling apparatus comprising:
    a handle assembly;
    a drive system operable supported in said handle assembly and constructed to impart drive motions and a retraction motion;
    a movable handle portion operably supported on said handle assembly and interfacing with said drive system such that manipulation of said movable handle causes said drive system to impart said drive motions;
    an elongated body protruding from said handle assembly and having a distal end couplable to a disposable loading unit, said disposable loading unit comprising:
       a carrier;
       a staple cartridge supported in said carrier;
       an anvil assembly movably coupled to said carrier for selective movable travel between open and closed positions relative to said staple cartridge;
       an axial drive assembly supported within said carrier to move in a distal direction from a start position to an end position through said carrier and said staple cartridge and move in a proximal direction from said end position to said start position;
       a motor supported within said carrier and interfacing with said axial drive assembly to drive said axial drive assembly in said distal and proximal directions;
       a battery holder movably supported within said carrier and interfacing with a control rod operably supported by said elongated body to receive said drive motions therefrom upon manipulation of said moveable handle portion; and
       a battery supported within said battery holder such that said battery is retained in a disconnected position prior to coupling said disposable loading unit to said distal end of said elongated body and said battery is movable therefrom to at least one connected position when said disposable loading unit is coupled to said distal end of said elongated body.

16. The surgical cutting and stapling apparatus of claim 15 further comprising means for stopping said motor when said axial drive assembly encounters resistance that exceeds a predetermined amount of resistance.

17. The surgical cutting and stapling apparatus of claim 16 wherein said means for stopping said motor comprises a current limiter operably coupled to said motor.

18. The surgical cutting and stapling apparatus of claim 15 further comprising:
    a first indicator on said disposable loading unit for indicating when said axial drive assembly is in a starting position;
    a second indicator on said disposable loading unit for indicating when said anvil is in said closed position; and
    a third indicator on said disposable loading unit for indicating when said axial drive assembly is in said end position.

* * * * *